US010173025B2

(12) United States Patent
Spandorfer et al.

(10) Patent No.: US 10,173,025 B2
(45) Date of Patent: Jan. 8, 2019

(54) AUTOMATED DRUG DELIVERY SYSTEMS

(71) Applicant: iDTx Systems, Inc., Charleston, SC (US)

(72) Inventors: Michael Spandorfer, Charleston, SC (US); Brad Anthony Niese, Southlake, TX (US); Jeffery D. Arnett, Gilbert, AZ (US); Joshua A. Butters, Chandler, AZ (US); Lane Michael Johnson, Chandler, AZ (US)

(73) Assignee: IDTX SYSTEMS, INC., Charleston, SC (US)

( * ) Notice: Subject to any disclaimer, the term of this patent is extended or adjusted under 35 U.S.C. 154(b) by 734 days.

(21) Appl. No.: 14/692,299

(22) Filed: Apr. 21, 2015

(65) Prior Publication Data

US 2015/0297859 A1   Oct. 22, 2015

Related U.S. Application Data

(60) Provisional application No. 61/981,996, filed on Apr. 21, 2014.

(51) Int. Cl.
*A61M 16/14* (2006.01)
*A61M 15/00* (2006.01)
(Continued)

(52) U.S. Cl.
CPC .......... *A61M 16/14* (2013.01); *A61M 15/009* (2013.01); *A61M 16/0816* (2013.01);
(Continued)

(58) Field of Classification Search
CPC .............. A61M 16/14; A61M 16/0816; A61M 15/009; A61M 15/0083; A61M 2205/332; A61M 15/08; A61M 16/16
See application file for complete search history.

(56) References Cited

U.S. PATENT DOCUMENTS 4,558,710 A   12/1985   Eichler
4,604,093 A   8/1986   Brown et al.
(Continued)

FOREIGN PATENT DOCUMENTS

GB          2055046        2/1981
WO      WO 98/31413 A1    7/1998

OTHER PUBLICATIONS

Ari et al., A Guide to Aerosol Delivery Devices for Respiratory Therapists, 2$^{nd}$ Edition, American Association for Respiratory Care, © 2009, Exemplary pp. 22, 24 and 34.
(Continued)

*Primary Examiner* — Timothy Stanis
(74) *Attorney, Agent, or Firm* — Myers Bigel, P.A.

(57) ABSTRACT

A system for delivering drug is provided. The system includes an adapter and a device. The adapter is configured to establish fluid communication with a gas conduit of a ventilator circuit. The device includes an actuation member and an actuator. The actuation member is configured to pivot. A canister containing drug is disposed between the adapter and the actuation member. The actuator is engaged to the actuation member such that the actuator selectively causes pivotal movement of the actuation member, causing the actuation member to apply pressure over the canister, thereby causing the canister to deliver drug into the adapter.

16 Claims, 18 Drawing Sheets

(51) Int. Cl.
*A61M 16/08* (2006.01)
*A61M 16/16* (2006.01)
*A61M 16/00* (2006.01)

(52) U.S. Cl.
CPC ....... *A61M 15/008* (2014.02); *A61M 15/0083* (2014.02); *A61M 16/16* (2013.01); *A61M 2016/0024* (2013.01); *A61M 2016/0033* (2013.01); *A61M 2205/106* (2013.01); *A61M 2205/332* (2013.01); *A61M 2205/502* (2013.01); *A61M 2209/082* (2013.01)

(56) References Cited

U.S. PATENT DOCUMENTS

| | | | |
|---|---|---|---|
| 4,819,629 A | 4/1989 | Jonson |
| 4,934,358 A | 6/1990 | Nilsson et al. |
| 4,984,158 A | 1/1991 | Hillsman |
| 5,002,048 A | 3/1991 | Makiej, Jr. |
| 5,020,527 A | 6/1991 | Dessertine |
| 5,103,814 A | 4/1992 | Maher |
| 5,178,138 A | 1/1993 | Walstrom et al. |
| 5,277,175 A | 1/1994 | Riggs et al. |
| 5,284,133 A | 2/1994 | Burns et al. |
| 5,297,543 A | 3/1994 | Larson et al. |
| 5,363,842 A | 11/1994 | Mishelevich et al. |
| 5,392,768 A | 2/1995 | Johansson et al. |
| 5,394,866 A | 3/1995 | Ritson et al. |
| 5,404,871 A | 4/1995 | Goodman et al. |
| 5,431,154 A | 7/1995 | Seigel et al. |
| 5,437,267 A | 8/1995 | Weinstein et al. |
| 5,438,982 A | 8/1995 | MacIntyre |
| 5,474,058 A | 12/1995 | Lix |
| 5,497,764 A | 3/1996 | Ritson et al. |
| 5,507,277 A | 4/1996 | Rubsamen et al. |
| 5,520,166 A | 5/1996 | Ritson et al. |
| 5,522,378 A | 6/1996 | Ritson et al. |
| 5,522,385 A | 6/1996 | Lloyd et al. |
| 5,542,410 A | 8/1996 | Goodman et al. |
| 5,544,647 A | 8/1996 | Jewett et al. |
| 5,560,353 A | 10/1996 | Willemot et al. |
| 5,564,414 A | 10/1996 | Walker et al. |
| 5,608,647 A | 3/1997 | Rubsamen et al. |
| 5,617,844 A | 4/1997 | King |
| 5,622,162 A | 4/1997 | Johansson et al. |
| 5,622,163 A | 4/1997 | Jewett et al. |
| 5,655,516 A | 8/1997 | Goodman et al. |
| 5,676,129 A | 10/1997 | Rocci, Jr. et al. |
| 5,694,919 A | 12/1997 | Rubsamen et al. |
| 5,724,957 A | 3/1998 | Rubsamen et al. |
| 5,743,252 A | 4/1998 | Rubsamen et al. |
| 5,755,218 A | 5/1998 | Johansson et al. |
| 5,770,585 A | 6/1998 | Kaufman et al. |
| 5,794,612 A | 8/1998 | Wachter et al. |
| 5,809,997 A | 9/1998 | Wolf |
| 5,826,570 A | 10/1998 | Goodman et al. |
| 5,881,716 A | 3/1999 | Wirch et al. |
| 5,967,141 A | 10/1999 | Heinonen |
| 6,012,450 A | 1/2000 | Rubsamen |
| 6,014,972 A | 1/2000 | Sladek |
| 6,079,413 A | 6/2000 | Baran |
| 6,116,234 A | 9/2000 | Genova et al. |
| 6,119,684 A | 9/2000 | Nöl et al. |
| 6,123,068 A | 9/2000 | Lloyd et al. |
| 6,138,669 A | 10/2000 | Rocci, Jr. et al. |
| 6,148,815 A | 11/2000 | Wolf |
| 6,202,642 B1 | 3/2001 | McKinnon et al. |
| 6,223,744 B1 | 5/2001 | Garon |
| 6,237,597 B1 | 5/2001 | Kovac |
| 6,260,549 B1 | 7/2001 | Sosiak |
| 6,318,361 B1 | 11/2001 | Sosiak |
| 6,325,062 B1 | 12/2001 | Sosiak |
| 6,358,058 B1 | 3/2002 | Strupat et al. |
| 6,390,088 B1 | 5/2002 | Nöhl et al. |
| 6,435,175 B1 | 8/2002 | Stenzler |
| 6,523,536 B2 | 2/2003 | Fugelsang et al. |
| 6,529,446 B1 | 3/2003 | de La Huerga |
| 6,557,552 B1 | 5/2003 | Cox et al. |
| 6,595,389 B2 | 7/2003 | Fuchs |
| 6,598,602 B1 | 7/2003 | Sjoholm |
| 6,615,825 B2 | 9/2003 | Stenzler |
| 6,631,716 B1 | 10/2003 | Robinson et al. |
| 6,651,844 B2 | 11/2003 | Tomaka et al. |
| 6,681,767 B1 | 1/2004 | Patton et al. |
| 6,684,880 B2 | 2/2004 | Trueba |
| 6,725,859 B1 | 4/2004 | Rothenberg et al. |
| 6,830,046 B2 | 12/2004 | Blakley et al. |
| 6,871,645 B2 | 3/2005 | Wartman et al. |
| 6,962,152 B1 | 11/2005 | Sladek |
| 7,191,777 B2 | 3/2007 | Band et al. |
| 7,198,044 B2 | 4/2007 | Trueba |
| 7,201,166 B2 | 4/2007 | Blaise et al. |
| 7,201,167 B2 | 4/2007 | Fink et al. |
| 7,347,200 B2 | 3/2008 | Jones et al. |
| 7,495,546 B2 | 2/2009 | Lintell |
| 7,549,421 B2 | 6/2009 | Levi et al. |
| 7,600,511 B2 | 10/2009 | Power et al. |
| 7,634,995 B2 | 12/2009 | Grychowski et al. |
| 7,748,382 B2 | 7/2010 | Denyer et al. |
| 7,905,230 B2 | 3/2011 | Schuler et al. |
| 8,151,794 B2 | 4/2012 | Meyer et al. |
| 2002/0069869 A1 | 6/2002 | Farmer |
| 2002/0069870 A1 | 6/2002 | Farmer |
| 2003/0200964 A1 | 10/2003 | Blakley et al. |
| 2004/0069301 A1 | 4/2004 | Bacon |
| 2004/0084050 A1 | 5/2004 | Baran |
| 2004/0107961 A1 | 6/2004 | Trueba |
| 2004/0138577 A1 | 7/2004 | Kline |
| 2004/0231667 A1* | 11/2004 | Horton .............. A61M 15/0065 128/202.13 |
| 2004/0255936 A1 | 12/2004 | Urbanus |
| 2005/0016528 A1* | 1/2005 | Aslin ................ A61M 15/0091 128/200.23 |
| 2005/0039746 A1 | 2/2005 | Grychowski et al. |
| 2005/0139211 A1 | 6/2005 | Alson et al. |
| 2005/0183725 A1 | 8/2005 | Gumaste et al. |
| 2005/0235987 A1 | 10/2005 | Smaldone et al. |
| 2005/0268908 A1 | 12/2005 | Bonney et al. |
| 2005/0274378 A1 | 12/2005 | Bonney et al. |
| 2006/0021614 A1 | 2/2006 | Wermeling et al. |
| 2006/0254581 A1 | 11/2006 | Genova et al. |
| 2007/0151560 A1 | 7/2007 | Price et al. |
| 2007/0173731 A1 | 7/2007 | Meka et al. |
| 2008/0009761 A1 | 1/2008 | Acker et al. |
| 2008/0308101 A1 | 12/2008 | Spandorfer |
| 2009/0120431 A1 | 5/2009 | Borgschulte et al. |
| 2009/0137920 A1 | 5/2009 | Colman et al. |
| 2012/0055472 A1* | 3/2012 | Brunnberg ........ A61M 15/0065 128/203.12 |
| 2013/0008436 A1* | 1/2013 | Von Hollen ...... A61M 15/0086 128/200.14 |
| 2014/0251330 A1* | 9/2014 | Collins ............. A61M 15/0086 128/203.14 |

OTHER PUBLICATIONS

Carrillo et al., Automated Metered Dose Inhaler Presentation #5, Vanderbilt University Department of Engineering, 11 pages, dated Apr. 7, 2004.

Carrillo et al., The Development of an Automatic Metered Dose Inhaler, Vanderbilt University Department of BioMedical Engineering, 32 pages, Apr. 27, 2004.

European Office Action Corresponding to European Patent Application No. 08770987.9; dated Feb. 28, 2014; 10 Pages.

International Search Report and Written Opinion for corresponding PCT Application No. PCT/US2008/066883, dated Oct. 1, 2008.

OHMEDA Project: Automated Metered-Dose Inhaler Deliver Device, Biomedical Engineering Design Projects, College of Engineering University of Wisconsin-Madison, printed from http://homepages.cae.wisc.edu/, printed Jul. 3, 2008, 4 pages, final poster presentation and demo stated to be date May 10, 2002.

Product Specification and Directions, Metered Dose Inhaler (MDI) Adapter, Instrumentation Industries, Inc., 2 pages, (Date of first

(56) References Cited

OTHER PUBLICATIONS publication unknown but for exam purposes only, is to be considered before the priority date of the instant application.).

\* cited by examiner

AUTOMATED DRUG DELIVERY SYSTEMS

RELATED APPLICATION

This application claims priority from U.S. Provisional Application No. 61/981,996, filed Apr. 21, 2014, the disclosure of which is hereby incorporated herein in its entirety.

BACKGROUND

The present disclosure, in general, relates to ventilators and drug delivery systems. More specifically, but not exclusively, this disclosure relates to systems and methods of automating actuation of a pressurized metered dose inhaler disposed in a ventilator circuit.

A mechanical ventilator is used for generating a controlled flow of gas into a patient's airway. Generally a set of flexible tubes, which may be part of a ventilator circuit, is used for establishing the flow of gas into the patient's airway. The flexible tubes may include an endotracheal or tracheostomy tube secured into a patient's upper respiratory tract. To aid in the treatment of ventilated patients, aerosolized medication may be administered to the ventilated patient.

Conventionally, aerosolized medication is delivered to the patient through a metered-dose inhaler canister. The canister is engaged to an adapter, which is in fluid communication with the ventilator circuit. Once the canister is engaged, a caregiver manually squeezes the canister and adapter together to enable releasing of one pre-measured dose of aerosolized medication into the ventilator circuit.

The caregiver should ideally administer the aerosolized medication as per prescription. Generally, the prescribed instructions may include time at which a first dose of the aerosolized medication has to be sprayed, number of sprays per dose and time between doses, among others. Apart from the above instructions, the caregiver has to keep a count of the number of doses left in the canister. Further, the caregiver may have to follow all of the above, not just for one patient, but a number of patients. Furthermore, the caregiver generally takes over these tasks at the beginning of his shift from one or more other caregivers, and hands over the tasks to one or more other caregivers at the end of his shift. Hence, effective administering of aerosolized medication to ventilated patients depends on diligence, records, and communications of not just one caregiver, but a team of caregivers.

Further, the caregiver has to synchronize each spray with the precise onset of inspiration. The caregiver is expected to wait approximately for at least 20-30 seconds between sprays, and repeat until the prescribed dose is delivered. It is but natural that, technique, proficiency, and patience vary among individual caregivers and, consequently, dose delivery are often delivered rapid-fire and at non-optimal timing, thereby reducing therapeutic efficacy.

In light of the foregoing discussion, there is a need for automating actuation of a pressurized metered dose inhaler disposed in a ventilator circuit.

SUMMARY

Some embodiments of the present invention are directed to a system for delivering drug. The system includes an adapter configured to establish fluid communication with a gas conduit of a ventilator circuit. The system includes a device. The device includes an actuation member and an actuator. A canister containing drug is disposed between the adapter and the actuation member. The actuation member is configured to pivot. The actuator is engaged to the actuation member such that the actuator selectively causes pivotal movement of the actuation member, causing the actuation member to apply pressure over the canister, thereby causing the canister to deliver drug into the adapter.

The system may include a housing. The housing may be configured to at least partially encase the actuation member. The housing may be configured to be engaged to the adapter. The adapter may include a housing engagement feature and the housing may include an adapter receiving feature. The engagement feature may be configured to engage the adapter receiving feature such that the adapter is releasably engaged with the housing.

In some embodiments, the actuation member includes: a contact member configured to interface with the canister; and a sensing member configured to sense the amount of force exerted on the canister. The contact member may apply pressure over the sensing member as a result of pivotal movement of the actuation member that causes the actuation member to apply pressure over the canister. The contact member may be configured to traverse towards the sensing member when the contact member is pressed against the canister. The actuation member may include an intermediate member, with the intermediate member disposed between the sensing member and the contact member. The traverse movement of the contact member towards the sensing member may be limited by the intermediate member.

In some embodiments, the actuation member is configured to pivot away from the adapter at least when the actuation member is not interfacing the canister.

In some embodiments, at least a portion of the actuation member disposed towards the actuator is heavier than a portion of the actuation member disposed towards the canister.

In some embodiments, the actuation member and the adapter are configured such that distance between the actuation member and the adapter is operatively altered. The actuation member and the adapter may be configured such that reduction of distance between the actuation member and the adapter is prevented once the force applied on the canister reaches a predefined threshold.

In some embodiments, the system includes a support member and a height adjustment member. The actuation member may be engaged with the support member. The support member may define a threaded hole. The height adjustment member may include a screw and a knob. The screw may include a shaft and a head. At least a part of the shaft may define a threaded portion configured to mate with the threaded hole of the support member. One of the head and the knob may include at least one engagement arm, and the other may define at least one engagement notch. The engagement arm may be received by the engagement notch such that: the engagement arm is engaged in the engagement notch, irrespective of the torque required for rotating the screw, when the knob is rotated in a first direction resulting in increasing of the distance; and the engagement arm is engaged in the engagement notch only until a particular limit of torque is applied to the head, and thereafter the engagement arm starts slipping with respect to the knob when the knob is rotated in a second direction resulting in decreasing of the distance.

In some embodiments, the system includes a controller that is configured to: (i) receive input from a gas flow sensor disposed in the gas conduit and/or the ventilator circuit; and (ii) direct the actuator to cause pivotal movement of the actuation member in response to receiving input from the gas flow sensor.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The subject matter relates to automating actuation of a pressurized metered dose inhaler disposed in a ventilator circuit. The following description illustrates the principles of the invention, which may be applied in various ways to provide many different alternative embodiments. This description is not meant to limit the inventive concepts.

The present technology may be employed in automating drug delivery. The present technology may provide automated actuation of a pressurized metered dose inhaler disposed in a ventilator circuit, and may also provide automated monitoring of drug delivered by the pressurized metered dose inhaler. While exemplary embodiments of the present technology have been shown and described in detail below, it will be clear to the person skilled in the art that changes and modifications may be made without departing from its scope. As such, that which is set forth in the following description and accompanying drawings is offered by way of illustration only and not as a limitation. In addition, one of ordinary skill in the art will appreciate upon reading and understanding this disclosure that other variations for the technology described herein can be included within the scope of the present technology.

Figure 1:
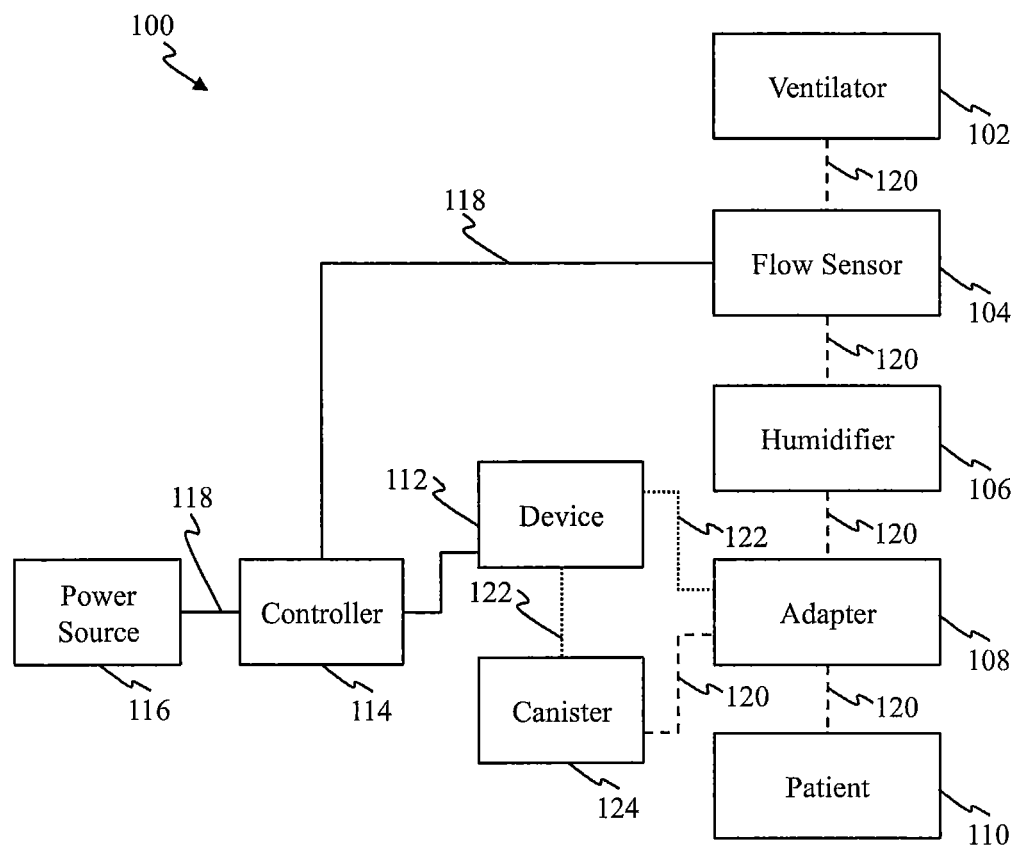
FIG. 1 is a schematic illustration of a system.

Referring to FIG. 1, a system 100 may be used for automated actuation of a pressurized metered dose inhaler disposed in a ventilator circuit. The system 100 may used for generating a controlled flow of gas into an airway of a patient 110. The system 100 may include a ventilator 102, a flow sensor 104, a humidifier 106, an adapter 108, a device 112, a controller 114, a power source 116 and a canister 124. Solid lines 1'18 may indicate at least cabling between elements of the system 100, dashed line 120 may indicate at least fluidic connection between the elements of the system 100, and dotted line 122 may indicate at least mechanical connection between the elements of the system 100.

The canister 124, which may be a metered dose inhaler, may be received by the device 112. The device 112 may be engaged with the adapter 108 such that the canister 124 is in fluidic communication with the adapter 108. The adapter 108 may be engaged with a tube, or a gas conduit of a ventilator circuit, such that the adapter 108 is in-line with the ventilator circuit. The tube with which the adapter 108 is engaged, may lead into the airway of the patient 110, in conjunction with arrangements required to establish such connection. The ventilator 102 may generate a controlled flow of gas into an airway of the patient 110. Gas from the ventilator 102 may flow through the flow sensor 104, the humidifier 106 and the adapter 108, and finally into the airway of the patient 110. It shall be noted that, the position of one or more elements in the path taken by the gas may be changed to an extent that is practically possible.

Automated actuation of the canister 124 may be enabled by providing instructions to the controller 114. The controller 114 may receive input from the flow sensor 104. The flow sensor 104 may be configured to provide input corresponding to the rate of flow of gas through a tube with which it is engaged. The controller 114 may use the input received by the flow sensor 104 to optimally time the actuation of the canister 124 by the device 112, to enable substantially optimal therapeutic efficacy. The controller 114 may be connected to a power source 116, which may supply the required electric energy for the controller 114 and the device 112 to function. The connection between the controller 114 and the device 112 may enable supply of electricity to the device 112. Further, the connection between the controller 114 and the device 112 may enable the device 112 to receive input from the controller 114. Furthermore, the connection between the controller 114 and the device 112 may enable the controller 114 to receive input from the device 112.

The device 112 may use the input received from controller 114 to actuate the canister 124, which may release a metered dose of medicine present in the canister 124 into the adapter 108. The metered dose of medicine received by the adapter 108 may travel through the tube and may eventually enter the airway of the patient 110.

The device 112 may include a device control module, an actuator and an actuation member. The device control module may be connected to the controller 114, enabling reception of electric energy, and sending input to and receiving input from, the controller 114. The device control module on receiving input from the controller 114 to actuate the canister 124, may be by pressing the canister 124 against the adapter 108, may trigger the actuator. The actuator on being triggered may initiate motion of the actuation member. The motion of the actuation member may press the canister 124 against the adapter 108. The pressing of the canister 124 against the adapter 108 may enable releasing of aerosolized medication from the canister 124 into the adapter 108, and the aerosolized medication may travel through the tube and may eventually enter the airway of the patient 110.

Figure 2A:
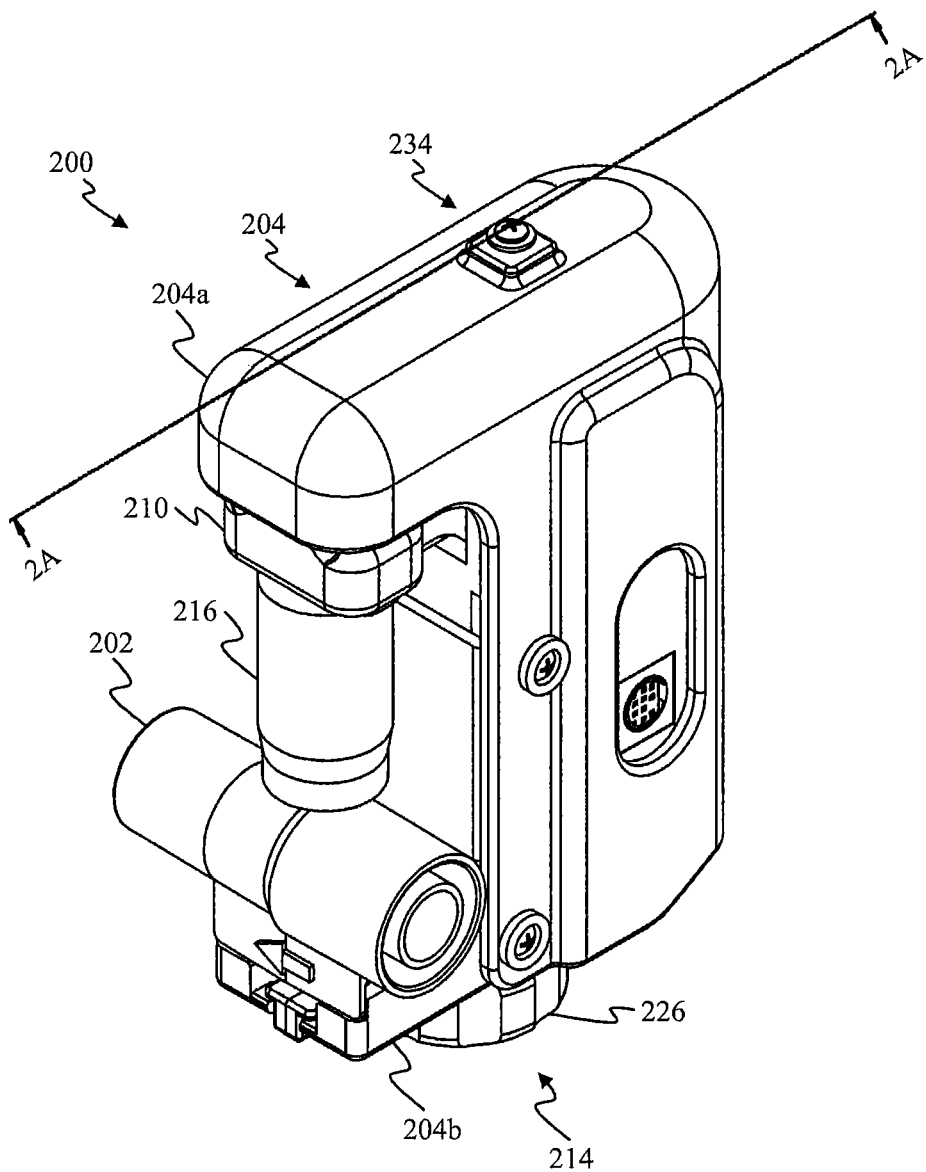
FIG. 2A is a perspective view of a device.
Figure 2B:
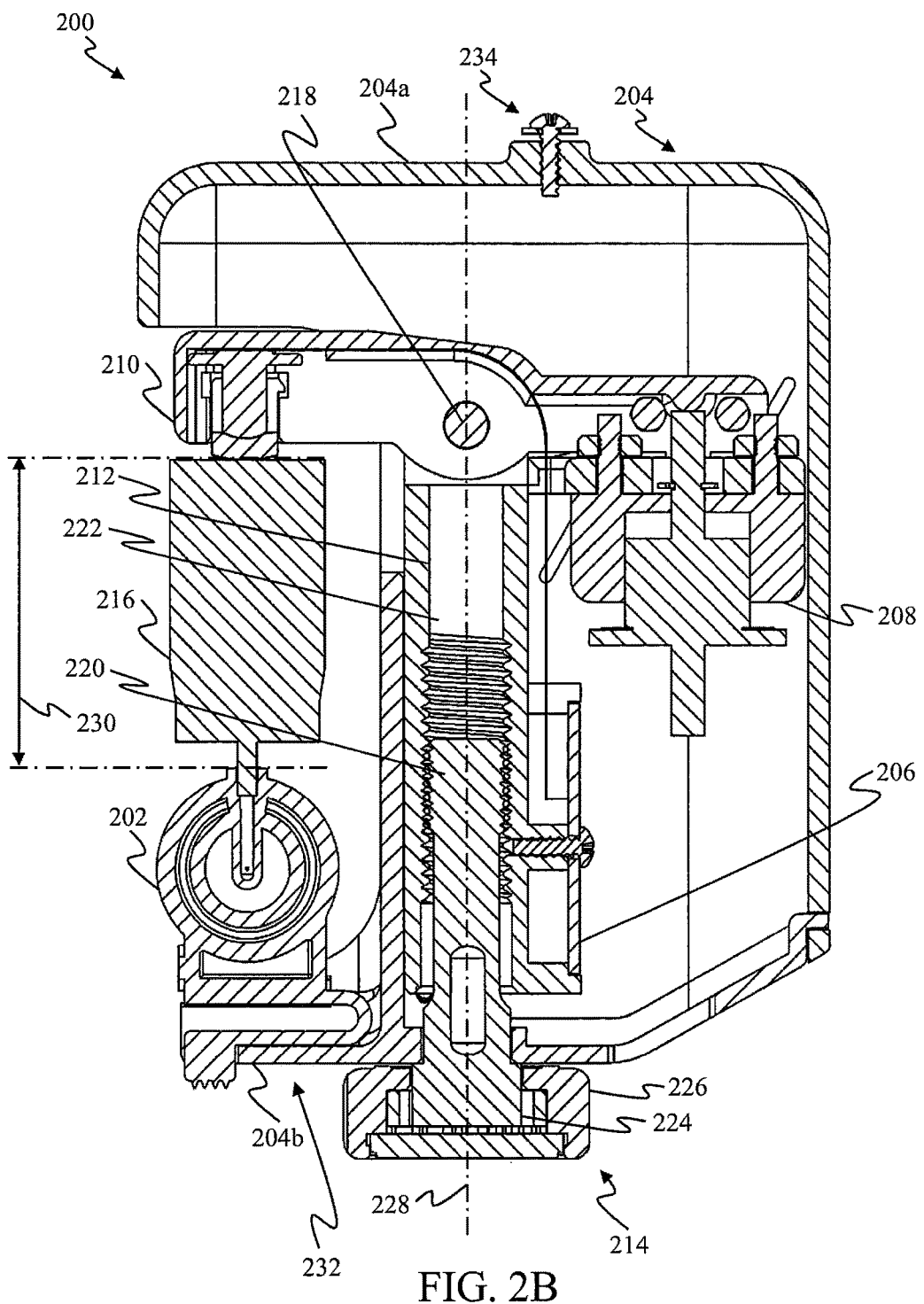
FIG. 2B is a cross sectional view of the device taken along lines 2A-2A of FIG. 2A.
Figure 3A:
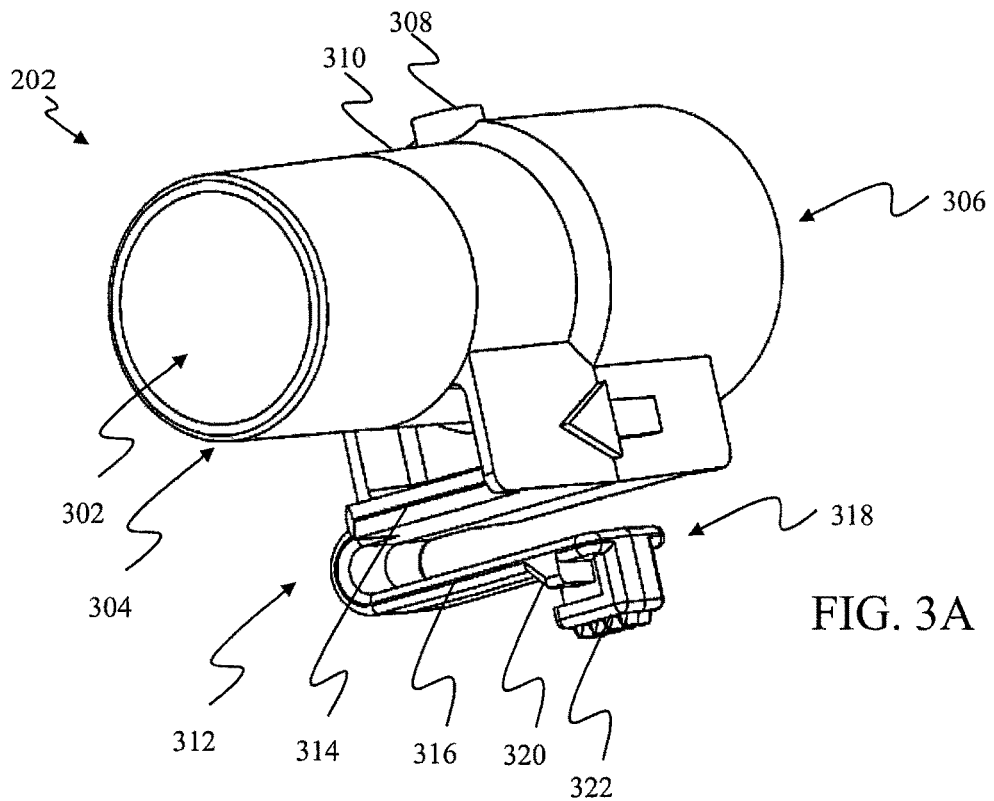
FIG. 3A is a perspective view of an adapter of FIG. 2A.
Figure 3B:
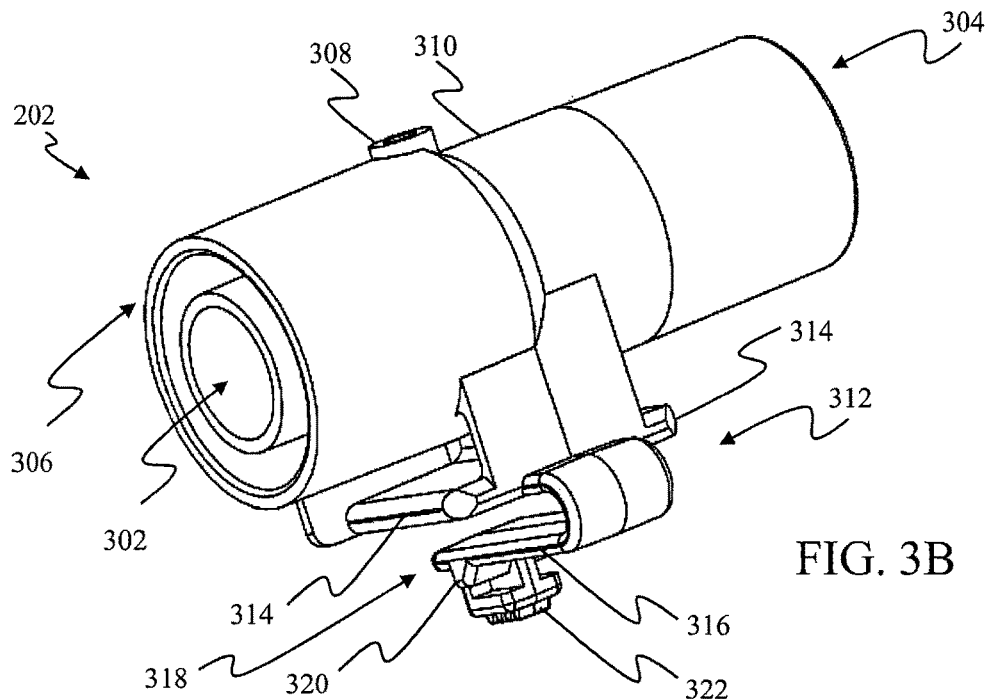
FIG. 3B is another perspective view of the adapter of FIG. 2A.
Figure 4:
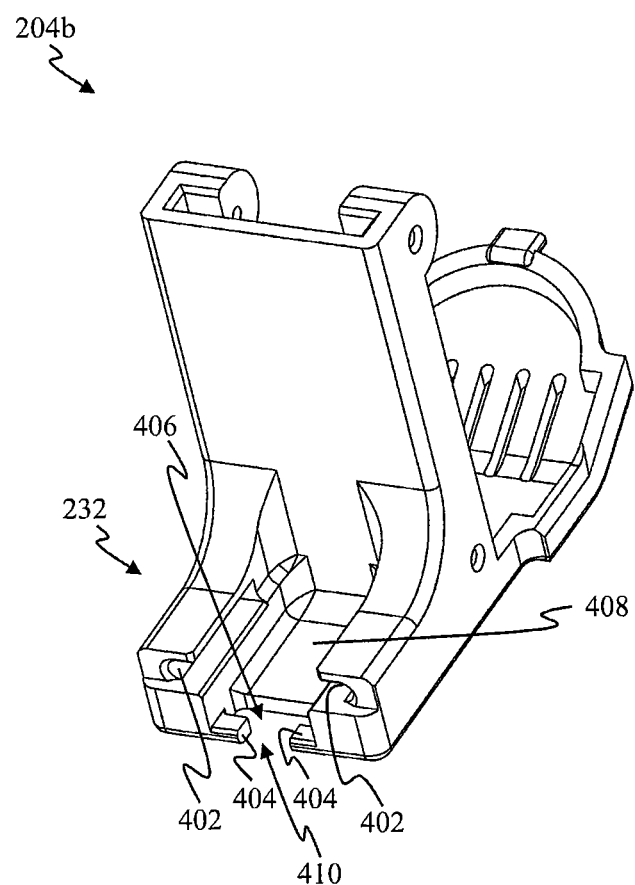
FIG. 4 is a perspective view of an adapter engaging member of the device of FIG. 2A.
Figure 5:
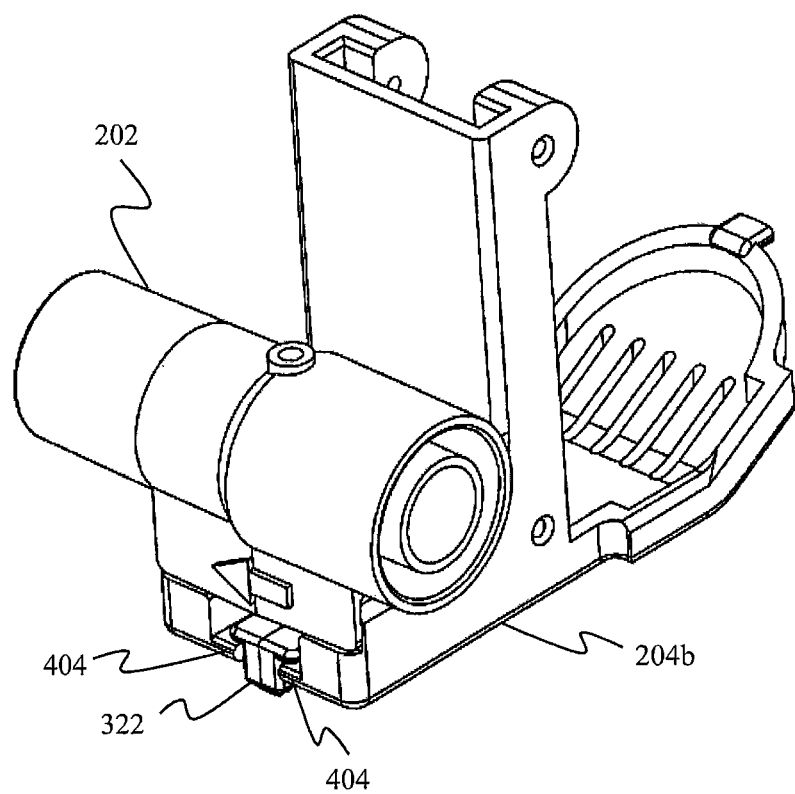
FIG. 5 is a perspective view of the adapter engaged with the adapter engaging member of the device of FIG. 2A.

Referring to FIGS. 2A and 2B, a device 200 may be used for automated actuation of a pressurized metered dose inhaler disposed in a ventilator circuit. The device 200 may be engaged with an adapter 202. The adapter 202 may be engaged with a tube of a ventilator circuit, such that the adapter 202 may be in-line with the tube, and therefore the ventilator circuit. The device 200 may include a housing 204, a device control module 206, an actuator 208, an actuation member 210, a support member 212 and a height adjustment member 214, among other components.

The device control module 206 may be connected to the controller 114, which may supply electricity and input to the device control module 206 for actuating. The device control module 206 may be at least electrically connected to the actuator 208. The actuator 208 may be mechanically engaged with support member 212. Further, the actuator 208 may be mechanically connected to the actuation member 210. The mechanical connection between the actuator 208 and the actuation member 210 may be such that, when the actuator 208 is triggered, the actuator 208 initiates pivotal motion in the actuation member 210. The pivotal motion may be such that a portion of the actuation member 210, which is proximal to a canister 216 engaged between the adapter 202 and the actuation member 210, moves towards the adapter 202. The actuation member 210 may also be engaged with the support member 212, such that, the actuation member 210 pivots about a pivot shaft 218 provided in the support member 212. The support member 212 may define a cavity 222 configured to receive a screw 220 of the height adjustment member 214. A head 224 of the screw 220 may be received by a knob 226. Rotation of the knob 226 may result in traverse movement of the support member 212 along the longitudinal axis 228 of the cavity 222 defined in the support member 212. The movement of the support member 212 may increase or decrease the distance 230 between the actuation member 210 and the adapter 202.

An operator may use the device 200 by engaging the device 200 with the adapter 202. The canister 216 is engaged with the device 200. The knob 226 may be rotated such that the actuation member 210 moves towards the canister 216 and interfaces the canister 216. Subsequently, when the device control module 206 receives an input to actuate the canister 216, the device control module 206 triggers the actuator 208. The actuator 208 pushes the actuation member 210. The actuation member 210 pivots about the pivot shaft 218, thereby pressing the canister 216 towards the adapter 202. Pressing of the canister 216 towards the adapter 202 may enable releasing of aerosolized medication from the canister 216 into the adapter 202.

Referring more specifically to FIGS. 3A-5, including FIG. 2, the adapter 202 may be configured to be engaged to the device 200. The adapter 202 may be engaged to the housing 204 of the device 200. The adapter 202 defines a through hole 302. A first end 304 of the adapter 202 at which the hole 302 begins, may be engaged with an end of a first tube, such that the hole defined in the first tube extends into the hole 302 defined by the adapter 202. Similarly, a second end 306 of the adapter 202, to which the hole 302 extends, may be engaged with an end of a second tube, such that the hole defined in the second tube extends into the hole 302 defined by the adapter 202. In effect, the hole 302 defined in the adapter 202 is in-line with the first and the second tube. The adapter 202 may further include a nozzle 308 extending through its wall 310. The nozzle 308 may be in fluid communication with the hole 302 defined by the adapter 202. The canister 216 may be engaged with the adapter 202 at or below the nozzle 308, such that, medication sprayed from the canister 216 enters a vertical channel in the adapter 202, is expelled through one or more central holes in the housing defining the vertical channel of the adapter 202, and enters the main channel of the adapter 202.

The adapter 202 may include an engagement feature 312 configured to be adapted with an adapter receiving feature 232 provided in an adapter engaging member 204b of the housing 204. The engagement feature 312 may include a shoulder member 314. A cantilever member 316 may extend from the shoulder member 314. The cantilever member 316 may have a narrower width as compared to the shoulder member 314. The cantilever member 316 may extend from one end of the shoulder member 314 and may extend towards an end of the shoulder member 314 that may be opposite to the end of the shoulder member 314 from which it extends. The configuration of the shoulder member 314 and the cantilever member 316 may define a "U" shaped cross section. Further, the configuration may enable the cantilever member 316 to be pushed towards the shoulder member 314, which may enable engagement of the adapter 202 with the housing 204 at the adapter receiving feature 232. Towards a free end 318 of the cantilever member 316, a pair of laterally extending fins 320 may be defined, which may prevent the adapter 202 from being disengaged from the device 200, unless the cantilever member 316 is operated to enable disengagement. Further, towards the free end 318 of the cantilever member 316, a holder 322 may be defined. An operator may use the holder 322 as a grip to push the cantilever member 316 towards the shoulder member 314, while engaging or disengaging the adapter 202 from the housing 204.

As mentioned earlier an adapter receiving feature 232 corresponding to the engagement feature 312 is provided in the adapter engaging member 204b. The adapter receiving feature 232 may define a pair of slots 402 configured to receive the shoulder member 314. Edges of the shoulder member 314 may be received by the slots 402. Further, the adapter engaging member 204b may include a platform 408 configured to interface with at least a part of the cantilever member 316 such that the part of the cantilever member 316 rests on the platform 408, thereby adding to the stability of the engagement between the adapter 202 and the device 200. The adapter engaging member 204b may further include a pair of block members 404, configured to interface with the fins 320 such that movement of the fins 320, once engaged, away from the device 200 is restricted. Further, the adapter engaging member 204b may define a holder cavity 406, configured to accommodate the holder 322. The holder cavity 406 may define a partially closed circumference. An opening in circumference may be defined by the gap 410 between the block members 404. The gap 410 may provide easy access to the holder 322, while disengaging the adapter 202 from the adapter receiving feature 232 (device 200).

To engage the adapter 202 with the adapter receiving feature 232 (device 200), the cantilever member 316 is pushed towards the shoulder member 314, by pushing the holder 322 towards the shoulder member 314. The shoulder member 314 is slid into the slots 402, thereafter, the holder 322 is released. The holder 322 is accommodated in the holder cavity 406, and the fins 320 interface the block members 404.

To disengage the adapter 202 from the adapter receiving feature 232 (device 200), the cantilever member 316 is pushed towards the shoulder member 314, by pushing the holder 322 towards the shoulder member 314. The shoulder member 314 is slid out of the slots 402, thereafter, the holder 322 is released.

Figure 6:
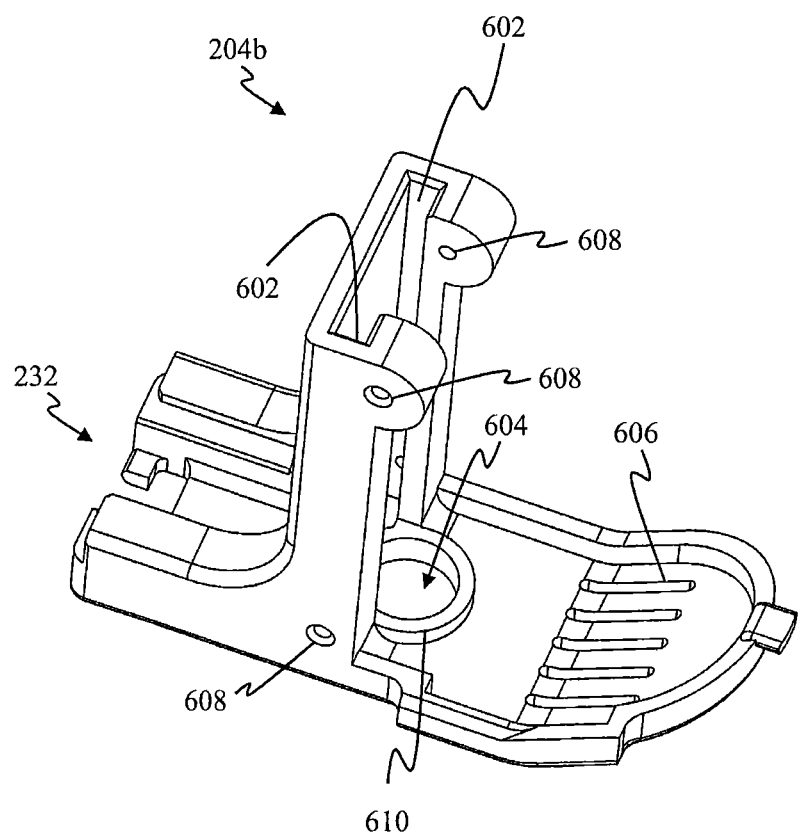
FIG. 6 is another perspective view of the adapter engaging member of the device of FIG. 2A.
Figure 7A:
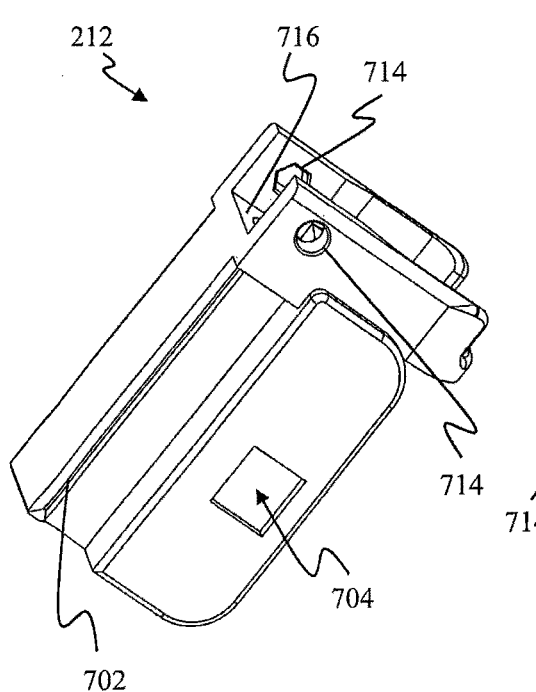
FIG. 7A is a perspective view of a support member of the device of FIG. 2A.
Figure 7B:
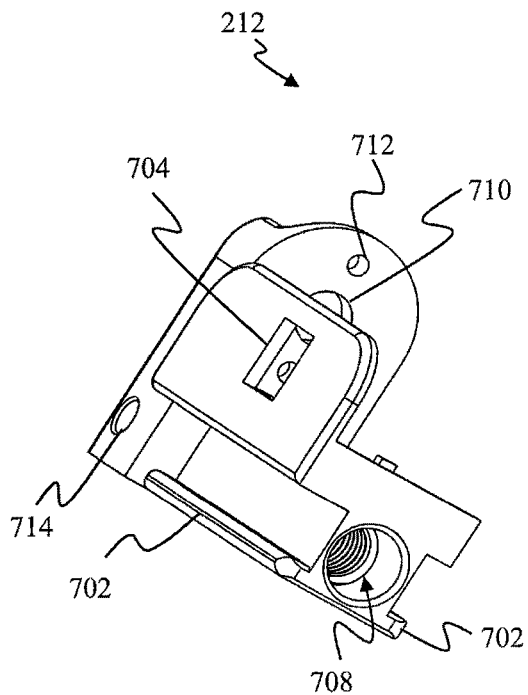
FIG. 7B is another perspective view of the support member of the device of FIG. 2A.
Figure 7C:
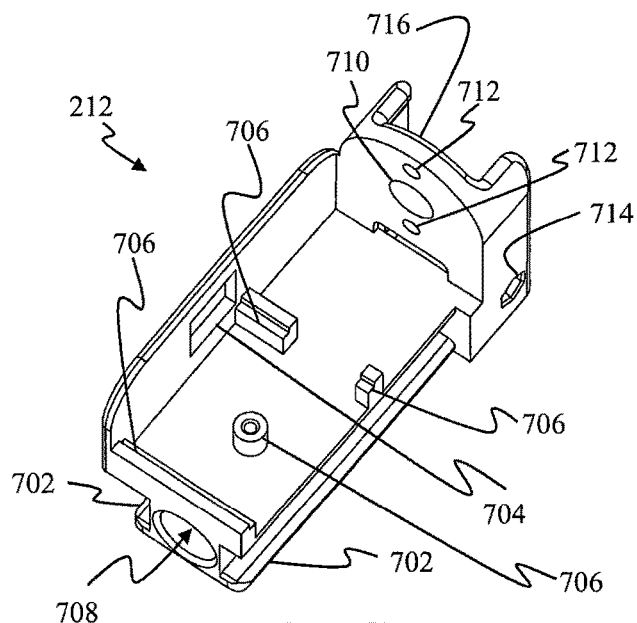
FIG. 7C is yet another perspective view of the support member of the device of FIG. 2A.

Referring also to FIGS. 6 to 7C, the adapter engaging member 204b may be configured to be engaged with the support member 212 and receive screw 220 of the height adjustment member 214. The adapter engaging member 204b defines an engagement slot 602 configured to receive a corresponding engagement shoulder 702 provided in the support member 212. Further, adapter engaging member 204b may define a screw receiving aperture 604 configured to receive the screw 220. A rim 610 may be provided around the screw receiving aperture 604. The rim 610 may be in the form of a projection extending in the superior direction. The rim 610 may interface with a retaining feature provided in the screw 220, and may restrict relative translational movement between the screw 220 and the adapter engaging member 204b. The adapter engaging member 204b may also define one or more ventilation openings 606, which may facilitate air circulation. Further, a plurality of fastening features 608 may be provided to enable the adapter engaging member 204b to be engaged with a cover member 204a of the housing 204.

Referring to FIGS. 7A-7C, the support member 212 may include an engagement shoulder 702, a window 704, a device control module accommodation feature 706, a threaded hole 708, a shaft accommodation aperture 710, an actuator engagement feature 712, a pivot shaft accommodation feature 714 and an actuation member receiving platform 716.

Referring to the prior figures, the engagement shoulder 702 may be configured to be received in the engagement slot 602 defined in the adapter engaging member 204b. It shall be noted that the engagement shoulder 702 may traverse in the engagement slot 602, thereby enabling the support member 212 to traverse when the height adjustment member 214 is operated.

The device control module accommodation feature 706 may be configured to engage the device control module 206 by a screw arrangement. The device control module 206 may be in the form of a board, such as a PCB. The window 704 may facilitate cable from the controller 114 to be engaged with the device control module 206.

The threaded hole 708 may align with the screw receiving aperture 604 defined in the adapter engaging member 204b. The screw receiving aperture 604 may be configured to receive the screw 220 of the height adjustment member 214, which may enable traverse movement of the support member 212.

The pivot shaft accommodation feature 714 may receive the pivot shaft 218, about which the actuation member 210 may pivot.

The actuator engagement feature 712 may enable engagement of the actuator 208 with the support member 212, using, for example, a nut and bolt arrangement. The shaft accommodation aperture 710 may be configured to receive a shaft provided in the actuator 208. The shaft of the actuator 208 may interface the actuation member 210, which may push the actuation member 210 when the actuator 208 is triggered.

Figure 8:
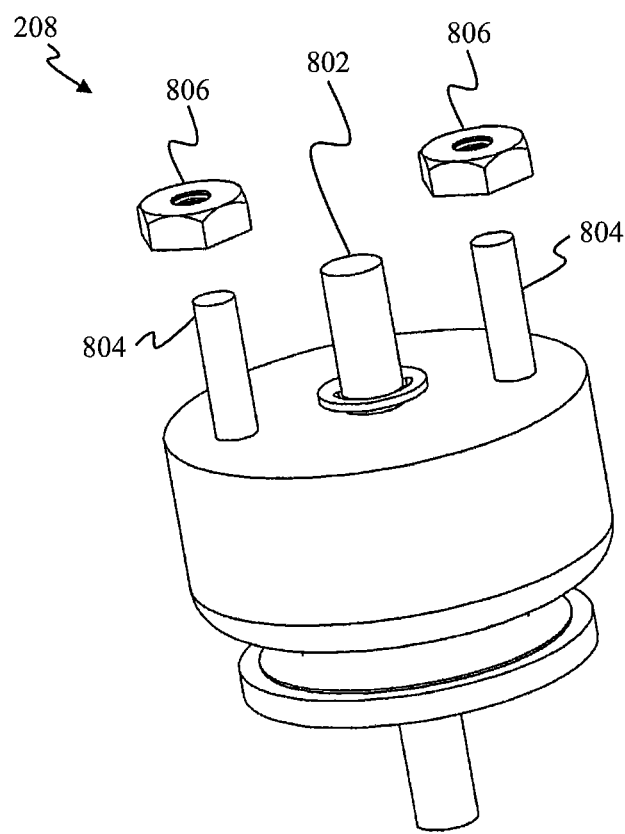
FIG. 8 is a perspective view of an actuator of the device of FIG. 2A.

Referring also to FIG. 8, the actuator 208 may include a shaft 802, a pair of engagement poles 804 and a pair of fasteners 806. The actuator 208 may be a solenoid actuator. The actuator 208 may be engaged with the support member 212, such that the shaft 802 is received by the shaft accommodation aperture 710 defined in the support member 212. The pair of engagement poles 804 may be received by the actuator engagement feature 712, thereafter, fasteners 806 may be secured to the pair of engagement poles 804, thereby engaging the actuator 208 with the support member 212. The shaft 802 of the actuator 208 may interface the actuation member 210, which may push the actuation member 210 when the actuator 208 is triggered.

Figure 9A:
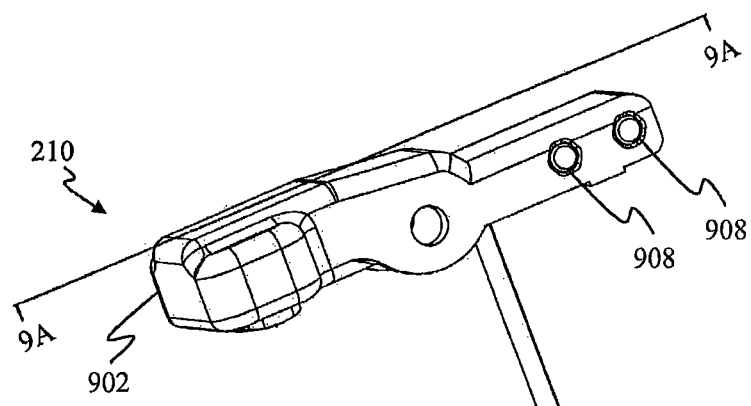
FIG. 9A is a perspective view of an actuation member of the device of FIG. 2A.
Figure 9B:
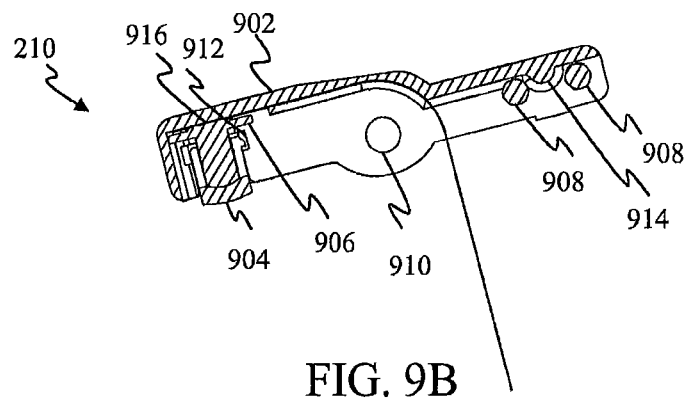
FIG. 9B is a cross sectional view of the actuation member of the device of FIG. 2A taken along lines 9A-9A of FIG. 9A.
Figure 9C:
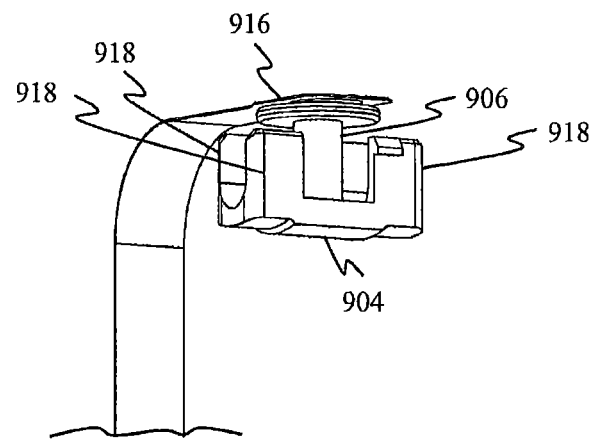
FIG. 9C is a perspective view of some of the components of the actuation member of the device of FIG. 2A.
Figure 10A:
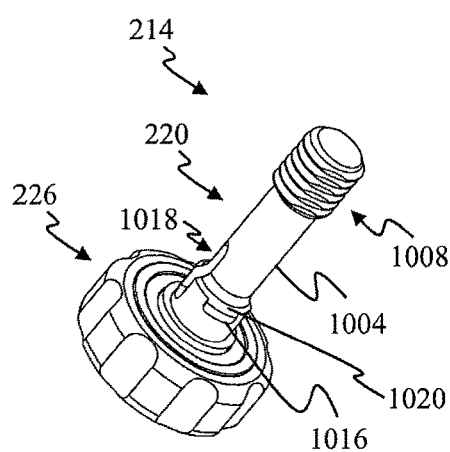
FIG. 10A is a perspective view of a height adjustment member of the device of FIG. 2.
Figure 10B:
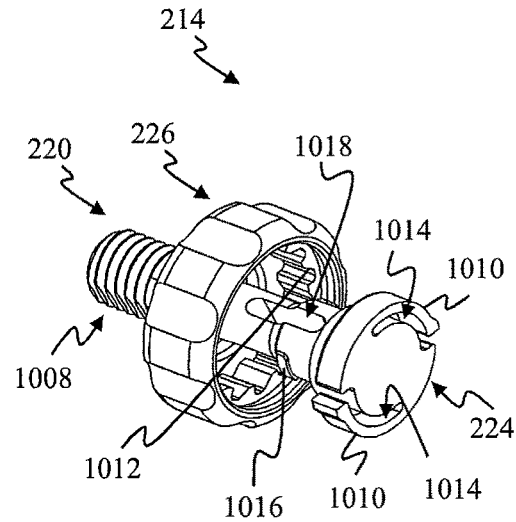
FIG. 10B is an exploded perspective view of the height adjustment member of the device of FIG. 2.
Figure 10C:
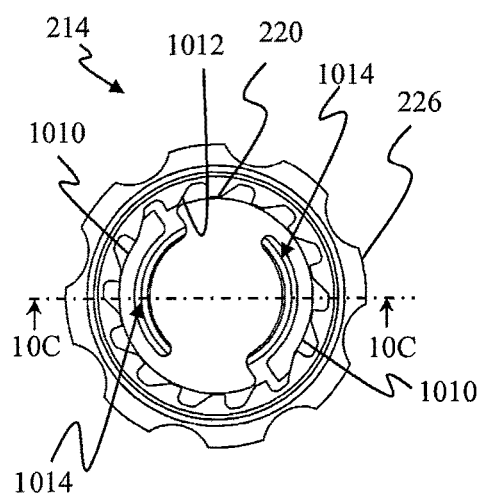
FIG. 10C is a bottom view of the height adjustment member of the device of FIG. 2.
Figure 10D:
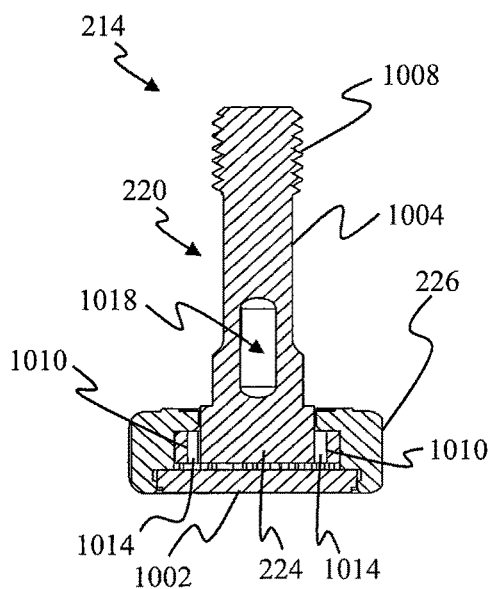
FIG. 10D is a cross sectional view of the height adjustment member of the device of FIG. 2A taken along lines 10C-10C of FIG. 10C.

Referring also to FIGS. 9A-9C, the actuation member 210 may include a body 902, a contact member 904, an intermediate member 906 and weight increasing members 908. The actuation member 210 may define a pivot shaft accommodation feature 910, a contact member traverse channels 912 and a shaft interfacing portion 914. The actuation member 210 may be configured to accommodate a sensing member 916.

The actuation member 210 may be engaged with the support member 212 at the pivot shaft accommodation feature 910. The pivot shaft accommodation feature 714 of the support member 212 aligns with the pivot shaft accommodation feature 910 of the actuation member 210, by receiving the pivot shaft 218. The shaft 802 of the actuator 208 interfaces the actuation member 210 at the shaft interfacing portion 914. The movement of the shaft 802 may translate into corresponding pivotal movement of the actuation member 210 about the pivot shaft 218.

The weight increasing members 908 may be disposed away from the contact member 904 and towards the shaft interfacing portion 914, thereby increasing the weight of the actuation member 210 towards the shaft interfacing portion 914. In effect, one objective of providing the weight increasing members 908 is to increase the weight of the actuation member 210 towards the shaft interfacing portion 914, which may be achieved using other suitable means (such as shifting the tilting pivot shaft accommodation feature 910 closer to the contact member 904 and further from the shaft interfacing portion 914). Increasing the weight may prevent the actuation member 210 from being tilted toward the adapter 202 when the actuation member is not interfacing the canister 216. Such prevention of tilting may enhance user experience while engaging the canister 216 with the device 200 by providing an open space in which the operator may insert the canister 216.

The contact member 904 may be received by the body 902 such that the contact member 904 interfaces the canister 216 at a top surface of the canister 216. The intermediate member 906 may be disposed at least to some extent over the contact member 904. Further, the sensing member 916 may be disposed over the intermediate member 906. The contact member 904 may include a plurality of arms 918. The arms 918 may be received by the contact member traverse channel 912 defined in the body 902, such that the contact member 904 traverses along the contact member traverse channels 912. It may be noted that, as the contact member 904 interfaces the canister 216 and is pushed by the canister 216, which may occur while decreasing the distance 230 between the adapter 202 and the actuation member 210, the contact member 904 traverses along the contact member traverse channels 912 and eventually contacts the intermediate member 906. As the contact member 904 pushes against the intermediate member 906, the force at which the intermediate member 906 is being pushed may be sensed by the sensing member 916, which may be disposed over the intermediate member 906. Pushing of the intermediate member 906 by the contact member 904 may occur in two circumstances. Pushing may occur while decreasing the distance 230 between the adapter 202 and the actuation member 210. Pushing may also occur when the actuation member 210 pivots to press the canister 216 towards the adapter 202, for enabling releasing of medicine. The sensing member 916 may be connected to the device control module 206, thereby facilitating communication of the data corresponding to the force sensed, to the controller 114. The data may be used, for example, to record actuation of the canister 216, monitoring, to judge sufficient or insufficient actuation and generate alerts if needed, among others.

It may be noted that, in order to disengage the canister 216 from the device 200, the distance 230 between the actuation member 210 and the adapter 202 may have to be increased, such that the actuation member 210 does not contact the canister 216. Similarly, when a new canister 216 may have to be engaged with the device 200, the distance 230 between the actuation member 210 and the adapter 202 may have to be decreased, such that the actuation member 210 establishes contact with the canister 216. The contact established may be such that the contact is not a mere touch interface, but an appropriate pressure is applied by the actuation member 210 over the canister 216. However, the pressure applied shall not be to such an extent that the canister 216 is "pre-actuated" to such an extent that triggering of the actuator 208 does not result in desired spraying of medicine from the canister 216. Such desired functionality may be provided by the height adjustment member 214.

Referring also to FIGS. 10A-10D, the height adjustment member 214 may enable adjustment of the distance 230 between the actuation member 210 and the adapter 202. The height adjustment member 214 may include the screw 220, the knob 226 and a cap 1002.

The screw 220 may include a shaft 1004 and a head 224. A part of the shaft 1004 may define a threaded portion 1008 configured to mate with the threaded hole 708 of the support member 212. The shaft 1004 may define a through slot 1018, which may extend across the longitudinal axis of the shaft 1004. The shaft 1018 may further include one or more retaining feature 1016. The retaining feature 1016 may be in the form of a projection. The retaining feature 1016 may be provided at a portion of the shaft 1004 that defines the slot 1018. A bottom surface of the retaining feature 1016 along with adjoining vertical surface the shaft 1004 may define a hard angle. On the other hand, the top surface of the retaining feature 1016 may define a sloped surface 1020. The sloped surface 1020 may enable sliding of the shaft 1004 into the screw receiving aperture 604 while engaging the screw 220 with the adapter engaging member 204b. The slot 1018 may enable compression of the shaft 1004 when the shaft 1004 is being snugly pushed through the screw receiving aperture 604, thereby facilitating engagement of the screw 220 with the adapter engaging member 204b. The bottom surface of the retaining feature 1016 may interface with the top surface of the rim 610 when the screw 220 is engaged with the adapter engaging member 204b, and may restrict relative translational movement between the screw 220 and the adapter engaging member 204b.

The head 224 of the screw 220 may be received by the knob 226. The cap 1002 may be secured to the knob 226 such that, pinch points existing between the head 224 and the knob 226 may be made inaccessible to a user.

The head 224 may include a pair of engagement arms 1010, and the knob may include a plurality of corresponding engagement notches 1012. The engagement arms 1010 and the engagement notches 1012 are configured such that, the engagement arms 1010 are engaged in the engagement notches 1012, irrespective of the torque required for rotating the screw 220, when the knob 226 is rotated in a first direction resulting in increasing of the distance 230. On the other hand, engagement arms 1010 and the engagement notches 1012 are configured such that the engagement arms 1010 are engaged in the engagement notches 1012 only until a particular limit of torque is applied to the head 224, thereafter the engagement arms 1010 start slipping with respect to the knob 226, when the knob 226 is rotated in a second direction resulting in decreasing of the distance 230. This feature may ensure that the canister 216 is not "pre-activated" to an undesired extent. The torque at which the engagement arms 1010 start to slip may be determined based on the desired pressure to be applied on the canister 216 when the actuation member 210 interfaces the canister 216 while reducing the distance 230.

Figure 13:
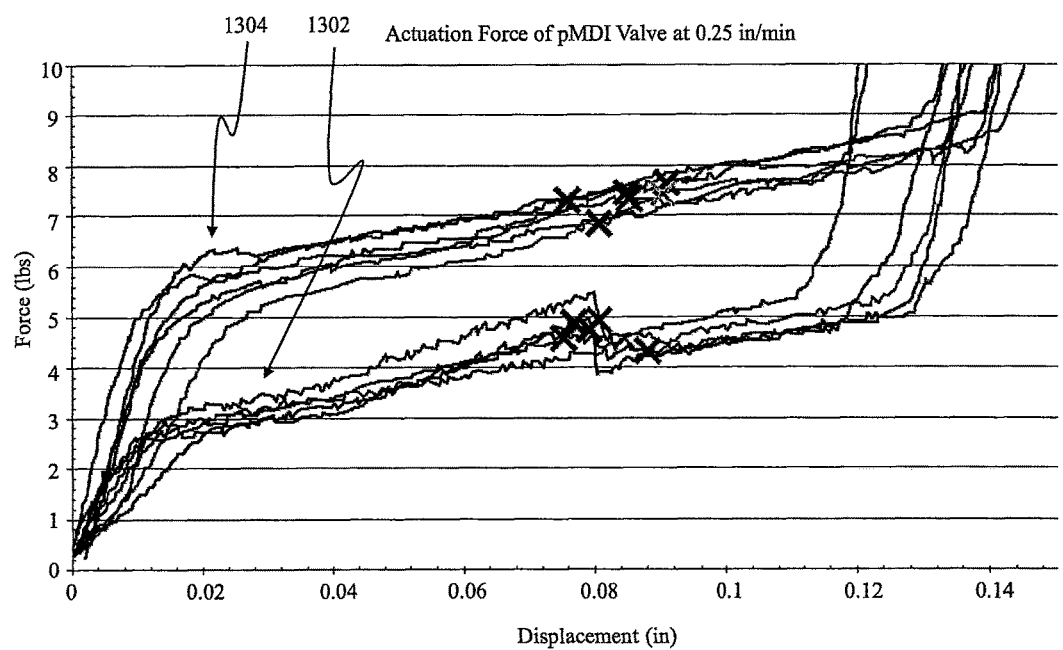
FIG. 13 is a graph illustrating relationship between force applied and displacement of valve provided in different types of canisters.

Referring to FIG. 13, the head may be designed such that only a desired amount of force is applied over the canister when the canister is engaged with the device. FIG. 13 is a graph illustrating relationship between force applied on canisters and displacement of valve provided in different types of canisters. Looking at the graph, one may infer that, valve provided in a first set 1302 of canisters may experience significant displacement at approximately 3 pounds of force. This may imply that spring in the valve may have been pre-loaded with about 3 pounds of force. Hence, the device may need to apply less than 3 pounds of force during setup to allow the pMDI valve to achieve its full range of travel. Hence, a force of, for example 1 pound may be applied when the canister is engaged with the device. Spraying may occur between 4 and 5 pounds in this group. Now referring to a second set 1304 of canisters, spraying may occur between 7 and 8 pounds, and displacement may end around 9 pounds of force. Hence, the device may be configured to apply at least 10 pounds of force to ensure complete actuation.

The above feature may be enabled by providing engagements arms 1010 that may semi-circularly extend, such that concentric gaps 1014 are defined in the head 224, thereby making the engagements arms 1010 flexible. Further, a surface of each engagement arms 1010 and the corresponding surface of each of the engagement notches 1012 that interface and transfer the torque from the knob 226 to the head 224, when rotated in a direction in which slipping is not desired, may be parallel to the diameter of the knob, or may be inclined to establish a locking or hugging interface, when rotated in the said direction.

Further, a surface of each engagement arms 1010 and the corresponding surface of each of the engagement notches 1012 that interface and transfer the torque from the knob 226 to the head 224, when rotated in a direction in which slipping is desired, may be inclined to define a slip-able or skid-able interface, thereby providing a ratchet mechanism effect. It may be noted that features of the knob 226 and the head 224 that enable slipping in one direction at a point where a particular higher torque is required to rotate the head 224, may be interchanged.

It may be noted that, desired flexibility of the engagement arms 1010 may be achieved by varying various parameters, such as, type of material used, amount of material used, shape of the arms, construction of the arms, configuration of the arms, configuration of interfacing surfaces and by providing grooves, among others.

In an embodiment, a level sensor may be provided in the device 200. The level sensor may be integrated with the device control module 206. The level sensor may be used to sense the level, orientation, and/or alignment of the device 200. It may be desirable to have the canister 216 aligned with the gravitational force, so that the medicine enters the adapter 202 adequately when the canister 216 is pressed. Data corresponding to the sensed level may be communicated to the controller 114, which may use the data for generating alerts, if required.

Figure 11A:
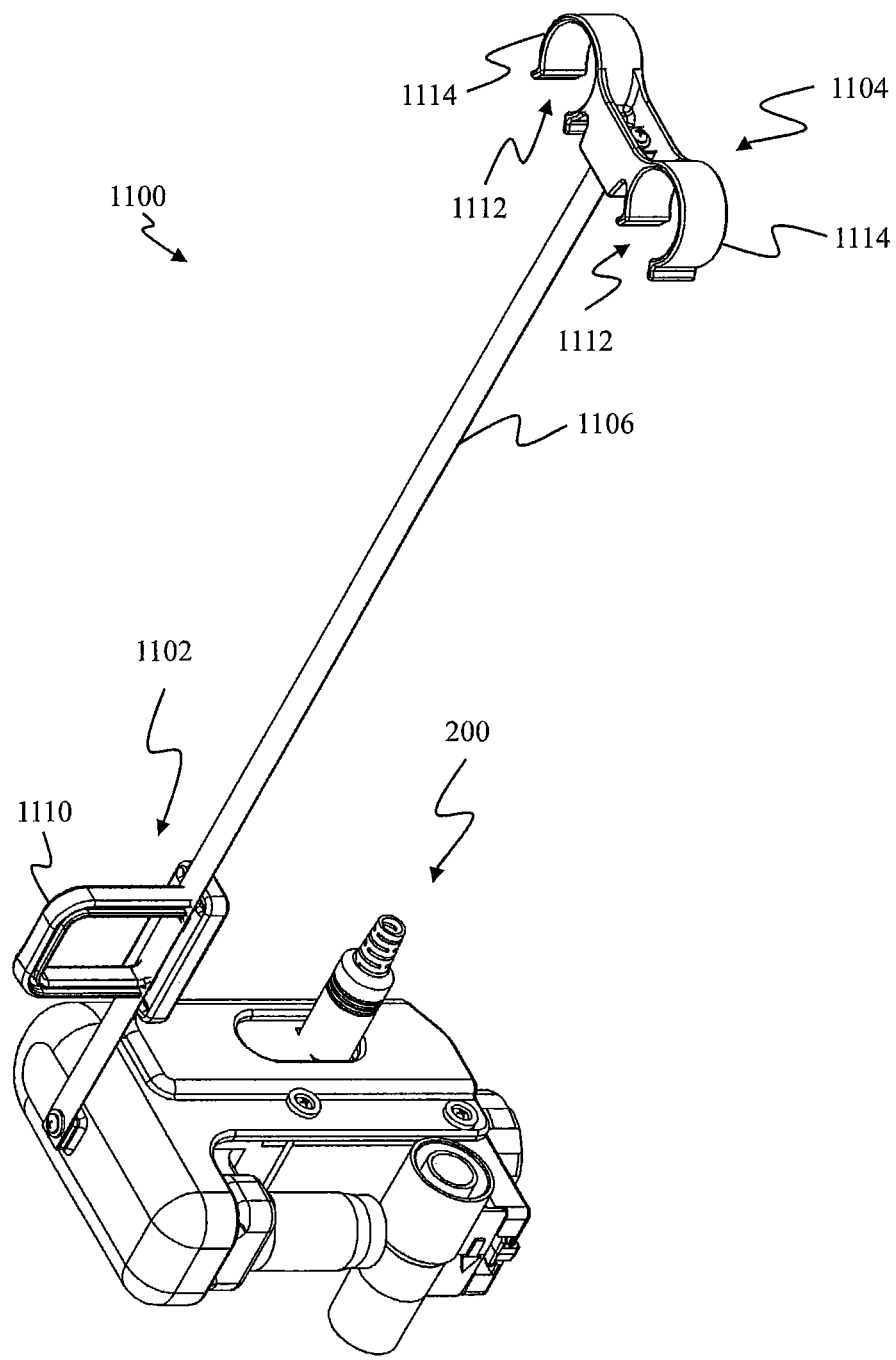
FIG. 11A is a perspective view of an alignment adjustment assembly.
Figure 11B:
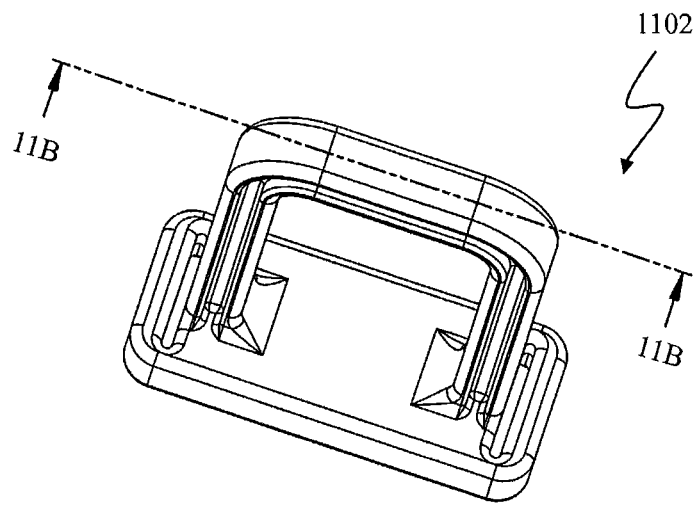
FIG. 11B is a perspective view of a hanger of the alignment adjustment assembly of FIG. 11A.
Figure 11C:
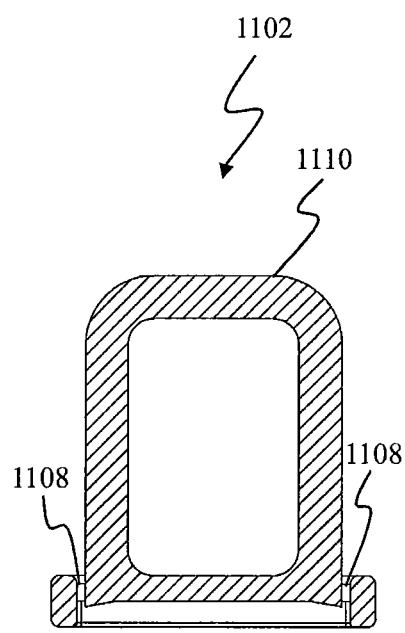
FIG. 11C is a cross sectional view of the hanger of the alignment adjustment assembly of FIG. 11A taken along lines 11B-11B of FIG. 11B.
Figure 12A:
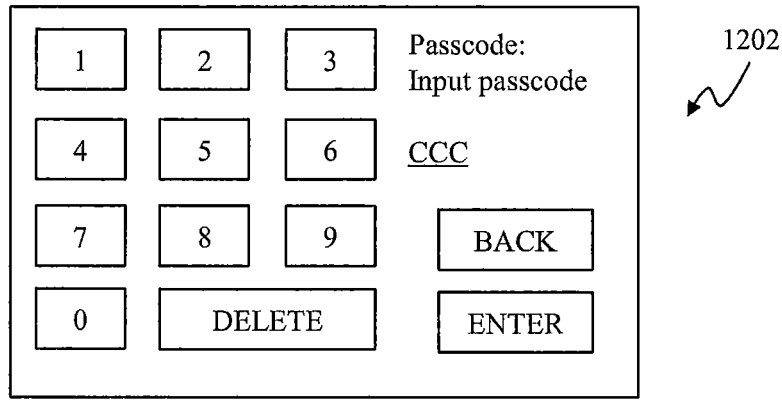
FIGS. 12A to 12F illustrate user interfaces provided by a controller.
Figure 12B:
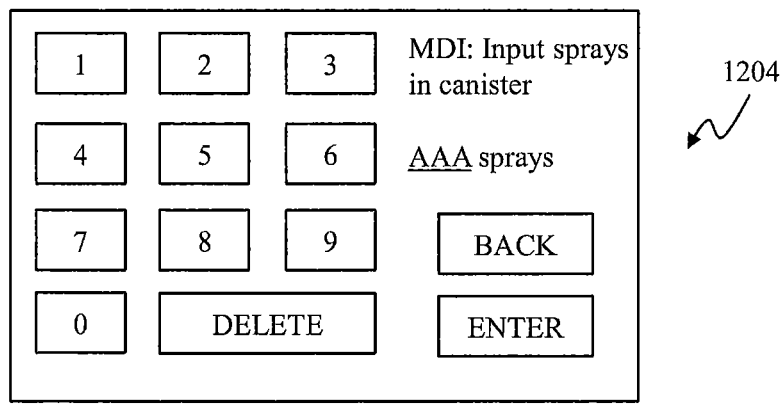
Figure 12C:
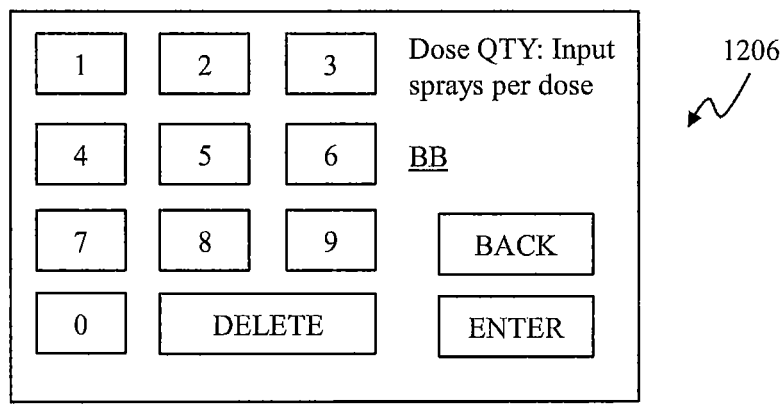
Figure 12D:
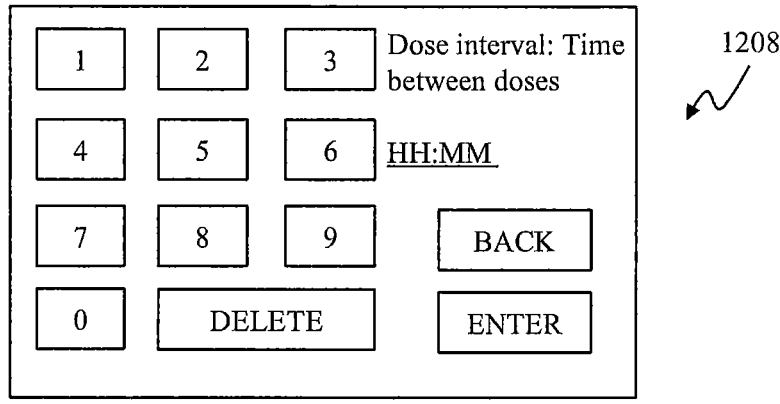
Figure 12E:
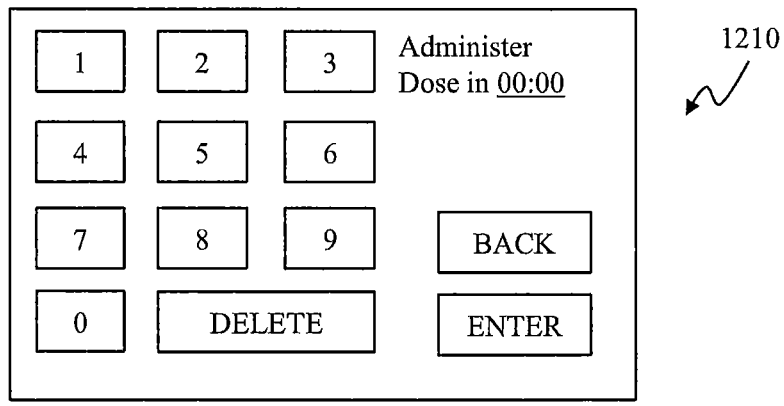
Figure 12F:
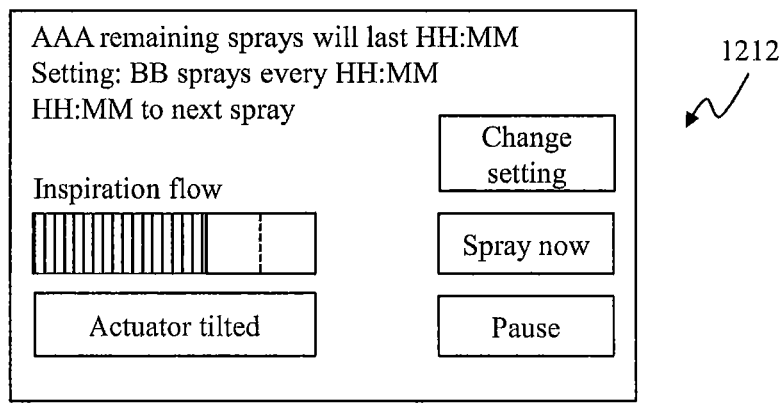

The alignment of the device 200 may be adjusted using an alignment adjustment assembly. Referring to FIGS. 11A and 11B, the alignment adjustment assembly 1100 may be used to adjust the alignment of the device 200. The alignment adjustment assembly 1100 may also substantially prevent the weight of the device 200 from being experienced by the patient 110. The alignment adjustment assembly 1100 may include a hanger 1102, a tube clip 1104 and a flexible member 1106. The flexible member 1106 may be engaged with the device 200. The flexible member 1106 may be engaged with the flexible member engagement feature 234 provided in the device 200. The flexible member 1106 engagement feature 234 may include a screw arrangement, and the flexible member 1106 may include a ring arrangement through which the screw may be passed and engaged with the device 200. The flexible member 1106 may connect the device 200, the hanger 1102 and the tube clip 1104. The arrangement may be such that the length of the flexible member 1106 between the device 200 and the hanger 1102, and the length of the flexible member 1106 between the hanger 1102 and the tube clip 1104 may be increased or decreased. In such an embodiment, the flexible member 1106 may be an adjustable strap.

The hanger 1102 may define a loop 1110, which may be engaged to a corresponding loop receiving structure, such as a hook. Alternatively, the hanger may define a hook, which may be engaged to a loop structure. Further, the hanger 1102 may define two slots 1108 through the flexible member 1106 may pass. The hanger 1102 may be slid along the flexible member 1106 to vary the distance between the hanger 1102 and the device 200, and the distance between the hanger 1102 and the tube clip 1104. It may be noted that length adjustment buckle may be provided in one or more of the device, the hanger and the tube clip.

The tube clip 1104 may include a pair of tube engagement structures 1114. Each of the tube engagement structures 1114 is configured to receive a tube and engage the same. The tube engagement structure 1114 may be semicircular, defining an opening 1112 through which the tube may be received. The opening 1112 may be smaller than the diameter of the tube and the surface of the tube engagement structure 1114 interfacing the tube may have a contour that may resemble the contour of the tube, so that the tube at least to some extent snugly fits into the tube engagement structure 1114 when engaged. The flexible member 1106 is engaged with the tube clip 1104 as well.

In addition to ensuring that the device is aligned accurately, it may also be necessary to ensure that the canister is actuated at the right instance. The right instance, apart from the dosage pattern that may be provided as an input to the controller, may also relate to the time at which the canister is actuated in relation to the patient's breathing pattern. The flow sensor may be placed at the ventilator in the inspiration line. The flow sensor detects the rate of flow of gas through the inspiration line and communicates data corresponding to the flow rate to the controller. The controller uses the data and instructs the device control module to actuate the canister at an instance, which may result in enhanced therapeutic efficacy.

Now referring to FIGS. 12A to 12F, a user interface may be provided in the controller 114. The user interface may be used to schedule dosage schedule, and may also be used to convey messages and/or alerts to users. An interface 1202 may be used to receive password ("CCC") from a user and provide access to various controls and settings. Once the access is granted, a user may change or input settings for administering medicine using the device. For example, an interface 1204 may be used to specify the number of sprays ("AAA") left in the canister that may be engaged with the device. An interface 1206 may be used to specify the number of sprays per dose ("BB"). An interface 1208 may be used to specify the time interval between doses ("HH:MM"). An interface 1210 may be used to specify the time at which the dose may be started ("00:00"). An interface 1212 may be used to impart a spray ("Spray now"), which may not have been scheduled previously. The interface 1212 may be used to pause the scheduled sprays ("Pause") or to change the settings. The interface 1212 may also be used to indicate air flow rate ("Inspiration flow"). The interface may also be used to provide various alerts.

The alerts may relate to alignment of the device, loading of the canister (force sensed after loading), actuation of the canister (force sensed upon actuation), replacement of canister based on number of sprays left and connection of the flow sensor, among others.

The controller may be configured to control a plurality of devices. The controller may also be configured to communicate data to external data processing devices, such as a smart phone, tablet, portable device, or other data processor. Further, the controller may be configured to be controlled from a remote location.

Figure 14A:
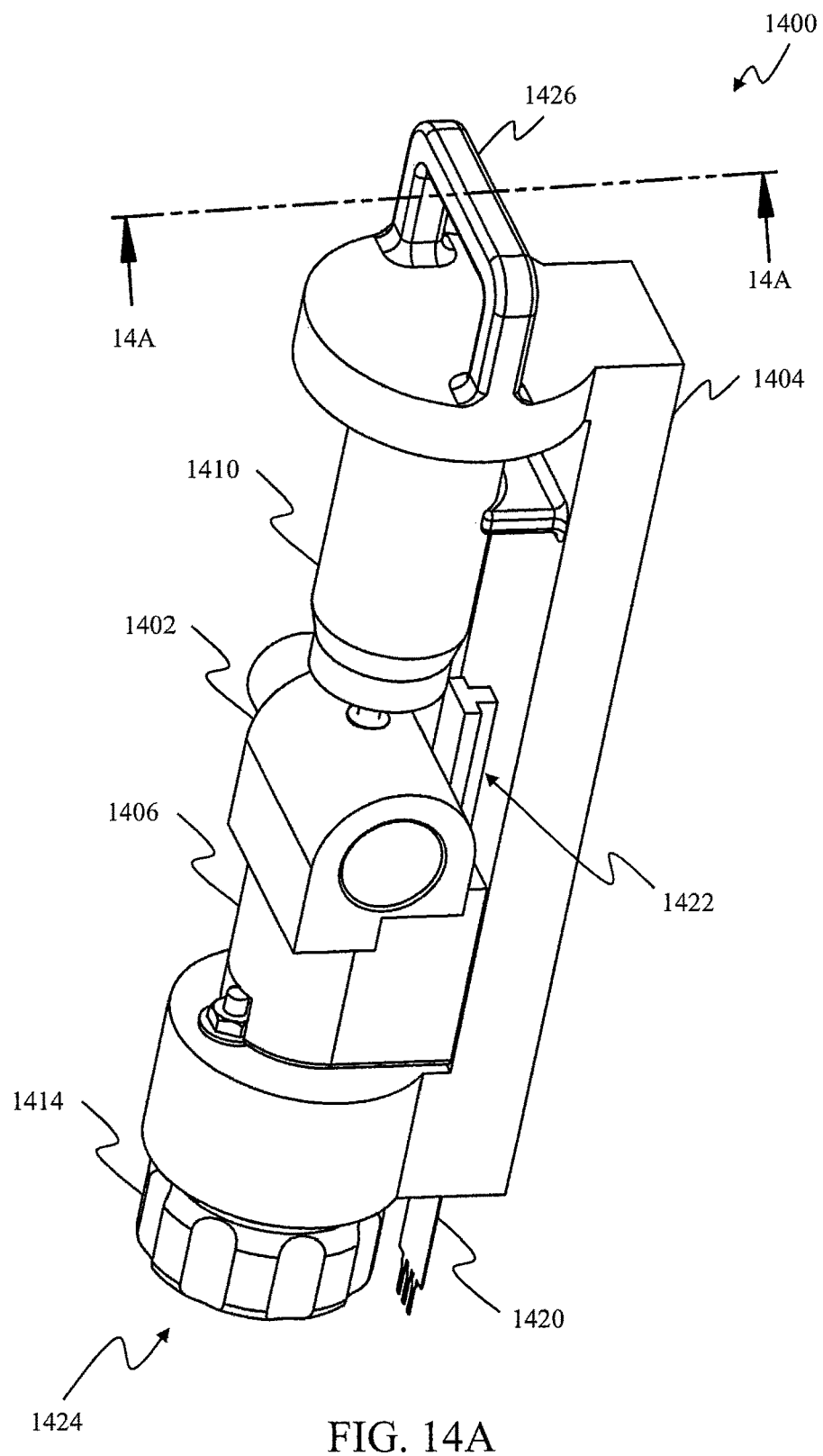
FIG. 14A is a perspective view of a device.
Figure 14B:
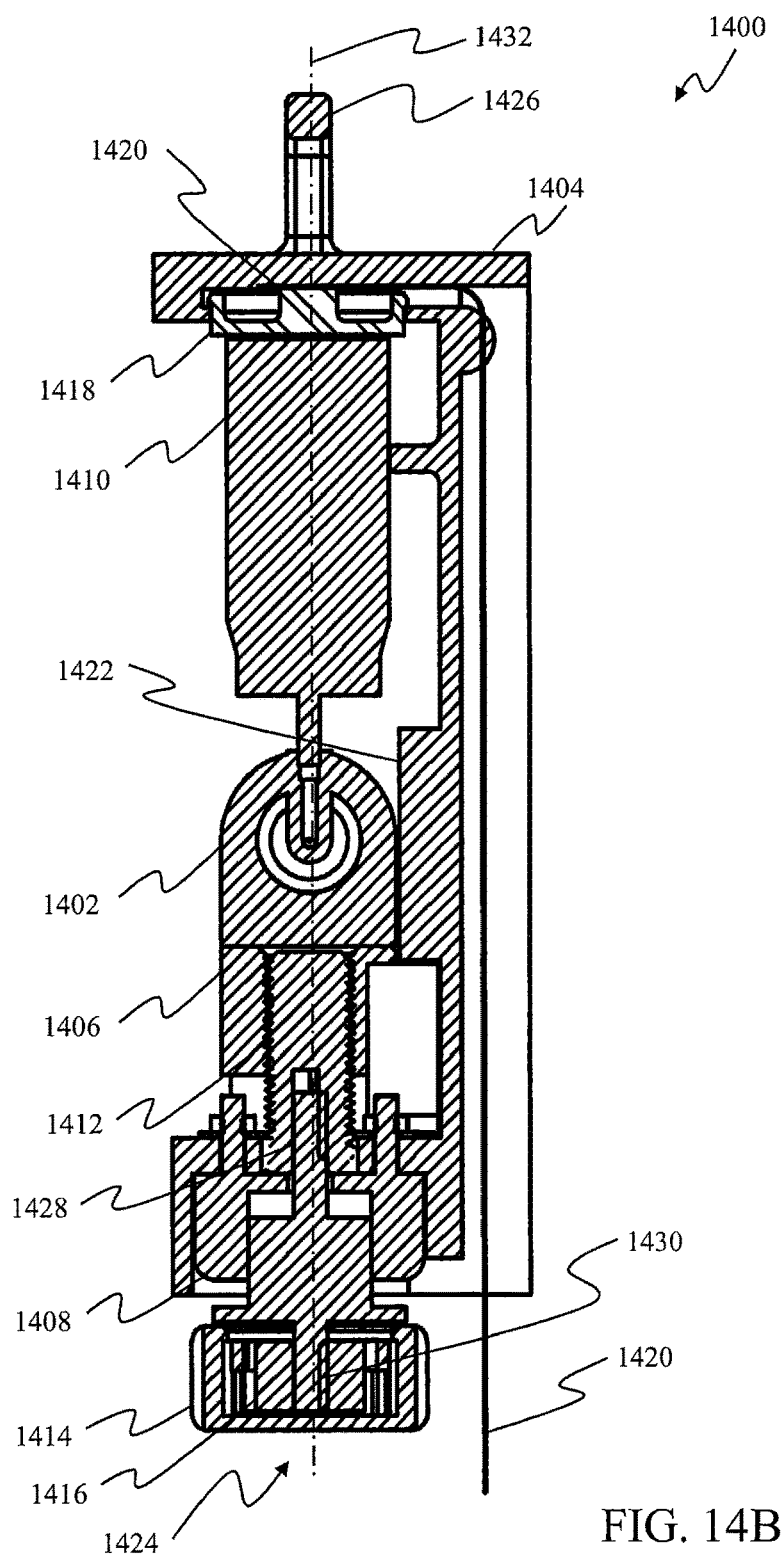
FIG. 14B is a cross sectional view of the device taken along lines 14A-14A of FIG. 14A.

Referring to FIGS. 14A and 14B, a device 1400 may be used for automated actuation of a pressurized metered dose inhaler disposed in a ventilator circuit. The device 1400 may be engaged with an adapter 1402. The device 1400 may include a housing 1404, an adapter engaging member 1406, an actuator 1408, a screw 1412, a height adjustment member 1424, a contact member 1418, a sensing member 1420 and a flexible member engagement feature 1426.

The device 1400 may further include a device control module, which may be connected to a controller, which may supply electricity and input to the device control module for actuating. The device control module may be at least electrically connected to the actuator 1408. The device control module may also be connected to the sensing member 1420.

A canister 1410 may be received by the device 1400 such that the canister 1410 is disposed between the adapter 1402 and the contact member 1418. The contact member 1418 may be received by the housing 1404 such that the contact member 1418 traverses along the longitudinal axis 1432 of the canister 1410 up to a pre-configured extent. The sensing member 1420 may be received by the housing 1404 such that the sensing member 1420 is disposed between the contact member 1418 and a portion of the housing 1404. Application of force on the contact member 1418 may be sensed by the sensing member 1420, as the contact member 1418 presses against the sensing member 1420.

The adapter 1402 is engaged with the adapter engaging member 1406. The adapter engaging member 1406 is configured to traverse along the axis 1432. The movement of the adapter engaging member 1406 may result in corresponding movement of the adapter 1402. For example, when the adapter engaging member 1406 moves towards the contact member 1418, the adapter 1402 also moves towards the contact member 1418, thereby applying force on the canister 1410. The adapter engaging member 1406 may traverse about a slot 1422, which may be defined by the housing 1404.

The adapter engaging member 1406 may define a threaded bore configured to receive the screw 1412. The screw 1412 may be received such that rotation of the screw 1412 or traverse movement of the screw 1412 may result in traverse movement of the adapter engaging member 1406.

The screw 1412 may be engaged with the actuator 1408. The actuator may include a shaft, and a first portion 1428 of the shaft may be engaged with the screw 1412. Further, a second portion 1430 of the shaft may be engaged with a head 1416 of the height adjustment member 1424. The head 1416 may be engaged with a knob 1414 of the height adjustment member 1424. The head 1416 and the knob 1414 may be engaged with each other such that head 1416 transfers the torque applied to the knob 1414 to the shaft only up-to a pre-configured limit when the knob 1414 is turned in a direction that decreases the distance between the adapter 1402 and the contact member 1418. However, head 1416 and the knob 1414 may be engaged with each other such that the head 1416 transfers the torque, irrespective of its extent, applied to the knob 1414 to the shaft, when the knob 1414 is turned in a direction that increases the distance between the adapter 1402 and the contact member 1418. The second portion 1430 of the shaft and the head 1416 may be engaged such that relative rotation between the second portion 1430 of the shaft and the head 1416 is prevented. Further, the first portion 1428 of the shaft and the screw 1412 may be engaged such that relative rotation between the first portion 1428 of the shaft and the screw 1412 is prevented. However, the first portion 1428 of the shaft may be allowed to traverse along the axis 1432. Triggering of the actuator 1408 may result in, the shaft of the actuator 1408 traversing along the axis 1432 towards the contact member 1418, which results in corresponding movement of the screw 1412 and the adapter engaging member 1406, thereby pressing the canister 1410. Pressing of the canister 1410 may enable releasing of aerosolized medication from the canister 1410 into the adapter 1402.

The components and devices disclosed herein may be made from metals, alloys, polymers, ceramics, glasses or composite materials. Different materials may be used for individual components. Different materials may be combined in a single component.

It should be understood that the present systems, apparatuses, and methods are not intended to be limited to the particular forms disclosed; rather, they are to cover all combinations, modifications, equivalents, and alternatives.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above described examples and embodiments may be mixed and matched to form a variety of other combinations and alternatives. It is also appreciated that this system should not be limited simply to automated actuation of a pressurized metered dose inhaler. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. A system for delivering drug, comprising:
an adapter configured to establish fluid communication with a gas conduit of a ventilator circuit, wherein the adapter comprises a first end and an opposite second end, the first end configured to engage a first tube of the gas conduit and the second end configured to engage a second tube of the gas conduit such that the adapter is in-line with the first and second tubes; and
a device comprising:
an actuation member, wherein the actuation member is configured to pivot, and wherein a canister containing a drug is disposed between the adapter and the actuation member; and
an actuator engaged to the actuation member such that the actuator is configured to selectively cause pivotal movement of the actuation member, causing the actuation member to apply pressure over the canister, thereby causing the canister to deliver the drug directly into the adapter;
wherein the actuation member comprises a contact member configured to interface with the canister, the system further comprising a height adjustment member comprising a rotatable member at a bottom portion of the device that is operatively connected to the actuation member, wherein the rotatable member is configured to be rotated in a first direction to move the actuation member in a first direction such that the contact member contacts the canister and in a second, opposite direction to move the actuation member in a second direction such that the contact member is spaced apart from the canister.

2. The system of claim 1, further comprising a housing, wherein the housing is configured to at least partially encase the actuation member, and wherein the housing is configured to be engaged to the adapter.

3. The system of claim 2, wherein the adapter comprises a housing engagement feature and the housing comprises an adapter receiving feature, and wherein the housing engagement feature is configured to engage the adapter receiving feature such that the adapter is releasably engaged with the housing.

4. The system of claim 1, wherein the actuation member comprises:
a housing; and
a sensing member between the housing and the contact member, the sensing member configured to sense an amount of force exerted on the canister.

5. The system of claim 4, wherein the contact member is configured to apply pressure over the sensing member as a result of pivotal movement of the actuation member that causes the actuation member to apply the pressure over the canister.

6. The system of claim 4, wherein the contact member is configured to traverse towards the sensing member when the contact member is pressed against the canister.

7. The system of claim 6, wherein the actuation member further comprises an intermediate member, wherein the intermediate member is disposed between the sensing member and the contact member, wherein movement of the contact member towards the sensing member is limited by the intermediate member.

8. The system of claim 1, wherein the actuation member is configured to pivot away from the adapter at least when the actuation member is not interfacing the canister.

9. The system of claim 1, wherein the actuation member is configured to pivot about a pivot shaft, and a portion of the actuation member disposed towards the actuator from the pivot shaft is heavier than a portion of the actuation member disposed towards the canister from the pivot shaft.

10. The system of claim 1, wherein the actuation member and the adapter are configured such that distance between the actuation member and the adapter is operatively altered.

11. The system of claim 10, wherein the actuation member and the adapter are configured such that reduction of distance between the actuation member and the adapter is prevented once a force applied on the canister reaches a predefined threshold.

12. The system of claim 1, further comprising a controller that is configured to: (i) receive input from a gas flow sensor disposed in the gas conduit and/or the ventilator circuit; and (ii) direct the actuator to cause pivotal movement of the actuation member in response to receiving input from the gas flow sensor.

13. The system of claim 1, wherein the adapter defines a longitudinal axis between the first and second ends of the adapter, and wherein the adapter longitudinal axis is parallel to a pivot axis of the actuation member.

14. The system of claim 1, further comprising a support member engaging the actuation member, wherein the rotatable member comprises a knob, and wherein the height adjustment member comprises a screw coupled to the knob and engaging the support member.

15. The system of claim 1, wherein the actuation member comprises:
a first end adjacent the canister;
a second end adjacent the actuator;
a pivot shaft between the first and second ends; and
at least one weight increasing member between the second end and the pivot shaft.

16. A system for delivering drug, comprising:
an adapter configured to establish fluid communication with a gas conduit of a ventilator circuit; and
a device comprising:
an actuation member, wherein the actuation member is configured to pivot, and wherein a canister containing a drug is disposed between the adapter and the actuation member; and
an actuator engaged to the actuation member such that the actuator is configured to selectively cause pivotal movement of the actuation member, causing the actuation member to apply pressure over the canister, thereby causing the canister to deliver the drug into the adapter,
wherein the actuation member and the adapter are configured such that distance between the actuation member and the adapter is operatively altered,
wherein the actuation member and the adapter are configured such that reduction of distance between the actuation member and the adapter is prevented once a force applied on the canister reaches a predefined threshold,
the system further comprising:
a support member, wherein the actuation member is engaged with the support member, and wherein the support member defines a threaded hole; and
a height adjustment member, wherein the height adjustment member comprises:
a screw comprising a shaft and a head, wherein at least a part of the shaft defines a threaded portion configured to mate with the threaded hole of the support member; and
a knob, wherein one of the head and the knob comprises at least one engagement arm, and the other defines at least one engagement notch, wherein the engagement arm is received by the engagement notch such that:
the engagement arm is engaged in the engagement notch, irrespective of the torque required for rotating the screw, when the knob is rotated in a first direction resulting in increasing of the distance between the actuation member and the adapter; and
the engagement arm is engaged in the engagement notch only until a particular limit of torque is applied to the head, and thereafter the engagement arm starts slipping with respect to the knob when the knob is rotated in a second direction resulting in decreasing of the distance between the actuation member and the adapter.

* * * * *